(12) United States Patent
Yoder et al.

(10) Patent No.: US 11,446,507 B2
(45) Date of Patent: Sep. 20, 2022

(54) FACILITATING TRUSTED PAIRING OF AN IMPLANTABLE DEVICE AND AN EXTERNAL DEVICE

(71) Applicant: Medtronic, Inc., Minneapolis, MN (US)

(72) Inventors: Matthew R. Yoder, Crystal, MN (US); Gary P. Kivi, Maple Grove, MN (US); Richard A. Sanden, Woodbury, MN (US); Bo Zhang, Blaine, MN (US); Eric D. J. Dorphy, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 312 days.

(21) Appl. No.: 16/693,463

(22) Filed: Nov. 25, 2019

(65) Prior Publication Data
US 2020/0094062 A1    Mar. 26, 2020

Related U.S. Application Data

(62) Division of application No. 15/443,269, filed on Feb. 27, 2017, now Pat. No. 10,493,287.

(51) Int. Cl.
*A61N 1/37* (2006.01)
*A61N 1/372* (2006.01)
(Continued)

(52) U.S. Cl.
CPC ........ *A61N 1/37252* (2013.01); *A61B 5/0031* (2013.01); *A61B 5/686* (2013.01);
(Continued)

(58) Field of Classification Search
None
See application file for complete search history.

(56) References Cited

U.S. PATENT DOCUMENTS

| 5,668,876 A | 9/1997 | Falk et al. |
| 7,350,230 B2 | 3/2008 | Forrest |

(Continued)

FOREIGN PATENT DOCUMENTS

| CN | 103997888 A | 8/2014 |
| EP | 3091459 B1 | 6/2020 |

OTHER PUBLICATIONS

Karani et al., "Implementation and Design Issues for Using Bluetooth Low Energy In Passive Keyless Entry Systems", IEEE, 2016, 6 Pages.

(Continued)

*Primary Examiner* — Ankit D Tejani
(74) *Attorney, Agent, or Firm* — Shumaker & Sieffert, P.A.

(57) ABSTRACT

Systems, apparatus, methods and computer-readable storage media facilitating trusted pairing between an implantable medical device (IMD) and an external device are provided. In one embodiment, an IMD includes a housing configured to be implanted within a patient, a memory and circuitry within the housing and a processor that executes executable components stored in the memory. The executable components can include: a communication component configured to initiate establishing a telemetry connection with an external device in accordance with a first telemetry protocol based on reception of a request, from the external device, to establish the telemetry connection with the IMD using the first telemetry protocol; and a validation component configured to restrict establishment of the telemetry connection with the external device in accordance with the first telemetry protocol based on reception of validation information from the external device, wherein provision of the validation information is excluded from the first telemetry protocol.

13 Claims, 13 Drawing Sheets

(51) Int. Cl.
*H04W 4/80* (2018.01)
*H04L 9/40* (2022.01)
*H04W 12/041* (2021.01)
*H04W 12/50* (2021.01)
*H04W 12/06* (2021.01)
*H04W 12/069* (2021.01)
*H04W 12/0431* (2021.01)
*A61B 5/00* (2006.01)

(52) U.S. Cl.
CPC .......... *A61N 1/37217* (2013.01); *H04L 63/18* (2013.01); *H04W 4/80* (2018.02); *H04W 12/041* (2021.01); *H04W 12/0431* (2021.01); *H04W 12/068* (2021.01); *H04W 12/069* (2021.01); *H04W 12/50* (2021.01); *A61N 1/37223* (2013.01)

(56) References Cited

U.S. PATENT DOCUMENTS

| | | |
|---|---|---|
| 9,168,383 B2 | 10/2015 | Jacobson et al. |
| 9,687,658 B2 | 6/2017 | Wu et al. |
| 9,855,433 B2 | 1/2018 | Shahandeh et al. |
| 9,894,691 B1 | 2/2018 | Hellman et al. |
| 2007/0123165 A1 | 5/2007 | Sheynman et al. |
| 2008/0003997 A1 | 1/2008 | Parkkinen et al. |
| 2008/0134281 A1 | 6/2008 | Shinde et al. |
| 2008/0312584 A1 | 12/2008 | Montgomery et al. |
| 2012/0108922 A1 | 5/2012 | Schell et al. |
| 2012/0172690 A1 | 7/2012 | Anderson et al. |
| 2012/0172941 A1 | 7/2012 | Rys |
| 2013/0029596 A1 | 1/2013 | Preston et al. |
| 2013/0214909 A1 | 8/2013 | Meijers et al. |
| 2013/0247194 A1 | 9/2013 | Jha et al. |
| 2014/0098956 A1 | 4/2014 | Hansen et al. |
| 2014/0143137 A1 | 5/2014 | Carlson |
| 2014/0188348 A1 | 7/2014 | Gautama et al. |
| 2014/0214104 A1 | 7/2014 | Greenhut et al. |
| 2014/0273824 A1 | 9/2014 | Fenner et al. |
| 2014/0298022 A1 | 10/2014 | Proennecke et al. |
| 2014/0330327 A1 | 11/2014 | Thompson-Nauman et al. |
| 2015/0133951 A1 | 5/2015 | Seifert et al. |
| 2015/0341785 A1 | 11/2015 | Young et al. |
| 2016/0050486 A1 | 2/2016 | Uggla |
| 2016/0250490 A1 | 9/2016 | Hoffman et al. |
| 2016/0374124 A1 | 12/2016 | Gothe et al. |
| 2017/0026777 A1 | 1/2017 | Denboer et al. |
| 2017/0056677 A1 | 3/2017 | Zhang et al. |
| 2017/0214631 A1 | 7/2017 | Zhang et al. |
| 2017/0216610 A1 | 8/2017 | Yoder et al. |
| 2017/0312530 A1 | 11/2017 | Schilling et al. |
| 2018/0021589 A1 | 1/2018 | Wu et al. |
| 2018/0028827 A1 | 2/2018 | Schilling et al. |

OTHER PUBLICATIONS (PCT/US2018/017969) PCT Notification of Transmittal of the International Search Report and the Written Opinion of the International Searching Authority, dated Apr. 16, 2018, 15 pages.

Chinese Office Action dated Jul. 5, 2021, corresponding to counterpart Chinese Patent Application No. 201880014042.7, 6 pages.

European Office Action dated Oct. 21, 2021, corresponding to counterpart, European Patent Application No. 18708010.6. 4 pages.

FACILITATING TRUSTED PAIRING OF AN IMPLANTABLE DEVICE AND AN EXTERNAL DEVICE

CROSS REFERENCE TO RELATED APPLICATIONS

This application is a Division of U.S. patent application Ser. No. 15/443,269, (U.S. Publication No. 2018/0243573), filed Feb. 27, 2017, the content of which is incorporated by reference in its entirety.

TECHNICAL FIELD

This disclosure relates generally to implantable devices and, more particularly, to systems, apparatus, methods and computer-readable storage media that facilitate trusted pairing between an implantable device and an external device.

BACKGROUND

Modern healthcare facilitates the ability for patients to lead healthy and full lives. Implantable medical devices (IMDs) are often utilized for such medical advances. For example, IMDs such as pacemakers, implantable cardio-verter-defibrillators (ICDs), neurostimulators, and drug pumps can facilitate management with a wide range of ailments, including, but not limited to, cardiac arrhythmias, diabetes, and Parkinson's disease. Patients and medical care providers can monitor the IMD and assess the current and historical physiological state of a patient to identify and/or predict impending events or conditions.

Implantable devices are transitioning from using proprietary telemetry technologies to using non-proprietary telemetry technologies such as, BLUETOOTH®, BLUETOOTH® low energy (BLE), Wireless Fidelity (Wi-Fi) protocol, and the like, as methods to interface with external devices. Transitioning to non-proprietary telemetry technologies can reduce cost by reducing or eliminating the need for expensive, proprietary instrumentation. These non-proprietary telemetry technologies can employ various mechanisms to establish a secure relationship between devices prior to allowing the devices to communicate certain information with one another using the non-proprietary telemetry communication protocol, a process referred to herein as "pairing." These pairing mechanisms are publically available in standard documents. As a result, additional security may be useful to initiate pairing and/or become paired with an implantable device that uses a non-proprietary telemetry communication protocol.

SUMMARY

The following presents a simplified summary of one or more of the embodiments in order to provide a basic understanding of one or more of the embodiments. This summary is not an extensive overview of the embodiments described herein. It is intended to neither identify key or critical elements of the embodiments nor delineate any scope of embodiments or the claims. Its sole purpose is to present some concepts of the embodiments in a simplified form as a prelude to the more detailed description that is presented later. It will also be appreciated that the detailed description can include additional or alternative embodiments beyond those described in the Summary section.

Embodiments described herein include systems, apparatus, methods and computer-readable storage media that facilitate ensuring trusted pairing between an implantable device and an external device. In some embodiments, the implantable device is or includes an IMD. In other embodiments, the implantable device is or includes a device configured to interact with the IMD. In these embodiments, both an implantable device and the IMD can be implanted within a patient.

In one embodiment, an IMD is provided. The IMD is configured to be at least partially implanted within a patient and includes a housing configured to be implanted at least partially within the patient, a memory, within the housing, that stores executable components, and circuitry, within the housing, and configured to at least one of obtain sensed physiological data associated with the patient or deliver a therapy to the patient. The IMD also includes a processor, within the housing, that executes the executable components stored in the memory. The executable components include at least a communication component configured to initiate establishing a telemetry connection with an external device in accordance with a first telemetry protocol based on reception of a request, from the external device, to establish the telemetry connection with the IMD using the first telemetry protocol. The executable components further include and a validation component configured to restrict establishment of the telemetry connection with the external device in accordance with the first telemetry protocol based on reception of validation information from the external device, wherein provision of the validation information is excluded from the first telemetry protocol.

In some implementations, the validation information indicates a remote server verified the external device or an entity operating the external device as being authorized to establish the telemetry connection with the IMD. In other implementations the validation information indicates an application of the external device determined an entity operating the external device is authorized to employ the external device to establish the telemetry connection with the IMD. For example, the application can be configured to determine the entity is authorized based on reception of input, via the external device, that uniquely identifies the entity as an authorized entity. Still in other implementations, the validation information comprises a signal received in accordance with a second telemetry protocol. For example, in some implementations the first telemetry protocol can comprise a non-proprietary telemetry protocol such as BLE and the second telemetry protocol can comprise a proprietary telemetry protocol, such as an induction based telemetry protocol. In other implementations, the first and second telemetry protocols can include different non-proprietary telemetry protocols. For example, the first telemetry protocol can comprise BLE and the second telemetry protocol can comprise near field communication (NFC), radio frequency identification (RFID), or the like.

In various additional implementations, the computer executable components can further include a negotiation component configured to negotiate one or more encryption keys with the external device in accordance with the first telemetry protocol in response to reception of the request, and associate the one or more encryption keys and an identifier for the external device with first data in the memory that characterizes the external device as potentially authorized to establish the telemetry connection with the IMD in accordance with the first telemetry protocol. The validation component can be further configured to associate the one or more encryption keys and the identifier with second data in the memory that characterizes the external device as authorized to establish the telemetry connection with the IMD in accordance with the first telemetry protocol, based on reception of the validation information. Based on association of the one or more encryption keys and the identifier with the second data, the communication component is configured to accept future requests from the external device to establish telemetry connections with the IMD using the first telemetry protocol without negotiating new encryption keys or requiring the external device to provide the validation information or new validation information.

In another embodiment, a method of communicating by an IMD configured to at least one of obtain sensed physiological data associated with a patient or deliver a therapy to the patient is provided. The method can include initiating, by the IMD, establishment of a trusted telemetry communication relationship with an external device in accordance with a defined telemetry protocol based on reception of a request, from the external device, to establish the trusted telemetry communication relationship with the IMD using the defined telemetry protocol. The method can further include restricting, by the IMD, the establishment of the trusted telemetry communication relationship with the external device in accordance with the defined telemetry protocol based on reception of validation information from the external device, wherein provision of the validation information is supplementary to the defined telemetry protocol. In one or more implementations, the establishment of the trusted telemetry communication relationship comprises negotiation of security information between the IMD and the external device, and wherein based on the establishment of the trusted telemetry communication relationship, the IMD is configured to accept requests from the external device to establish telemetry connections with the IMD using the defined telemetry protocol without negotiating new security information and without requiring the external device to provide the validation information or new validation information.

In another embodiment, a non-transitory computer readable medium is provided that comprises computer executable instructions that, in response to execution, cause an IMD including at least one processor to perform operations. The operations can include receiving a request from an external device to establish a telemetry link with the IMD using a telemetry protocol, and based on the receiving the request, determining whether the external device is associated with data in a memory of the IMD that characterizes the external device as a trusted device, wherein association of the external device with the data indicates the IMD previously received validation information from the external device in association with a pairing procedure performed between the IMD and the external device according to the telemetry protocol, and wherein the validation information is not defined by the telemetry protocol. In some implementations, the operations further comprise establishing the telemetry link with the external device using the telemetry protocol based on a determination that the external device is associated with the data. In other implementations, the operations further comprise forgoing establishing the telemetry link with the external device based on a determination that the external device is not associated with the data.

Still in another embodiment, a system is disclosed that comprises a device configured to perform telemetry communication with other devices using a non-proprietary telemetry protocol, and an IMD. The IMD can include a memory that stores executable components, and a processor that executes the executable components stored in the memory. These executable components can comprise a communication component configured to facilitate establishing a telemetry connection with the device in accordance with the non-proprietary telemetry protocol based on reception of a request, from the device, to establish the telemetry connection with the IMD using the non-proprietary telemetry protocol. These executable components can further comprise a validation component configured to restrict establishment of the telemetry connection with the device in accordance with the non-proprietary telemetry protocol based on reception of validation information from the device, wherein provision of the validation information by the device is excluded from the non-proprietary telemetry protocol.

Other embodiments and various non-limiting examples, scenarios and implementations are described in more detail below. The following description and the drawings set forth certain illustrative embodiments of the specification. These embodiments are indicative, however, of but a few of the various ways in which the principles of the specification can be employed. Other advantages and novel features of the embodiments described will become apparent from the following detailed description of the specification when considered in conjunction with the drawings.

DETAILED DESCRIPTION

The following detailed description is merely illustrative and is not intended to limit embodiments and/or application or uses of embodiments. Furthermore, there is no intention to be bound by any expressed or implied information presented in the preceding Technical Field, Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Additionally, the following description refers to components being "connected" and/or "coupled" to one another. As used herein, unless expressly stated otherwise, the terms "connected" and/or "coupled" mean that one component is directly or indirectly connected to another component, mechanically, electrically, wirelessly, inductively or otherwise. Thus, although the figures may depict example arrangements of components, additional and/or intervening components may be present in one or more embodiments.

Figure 1:
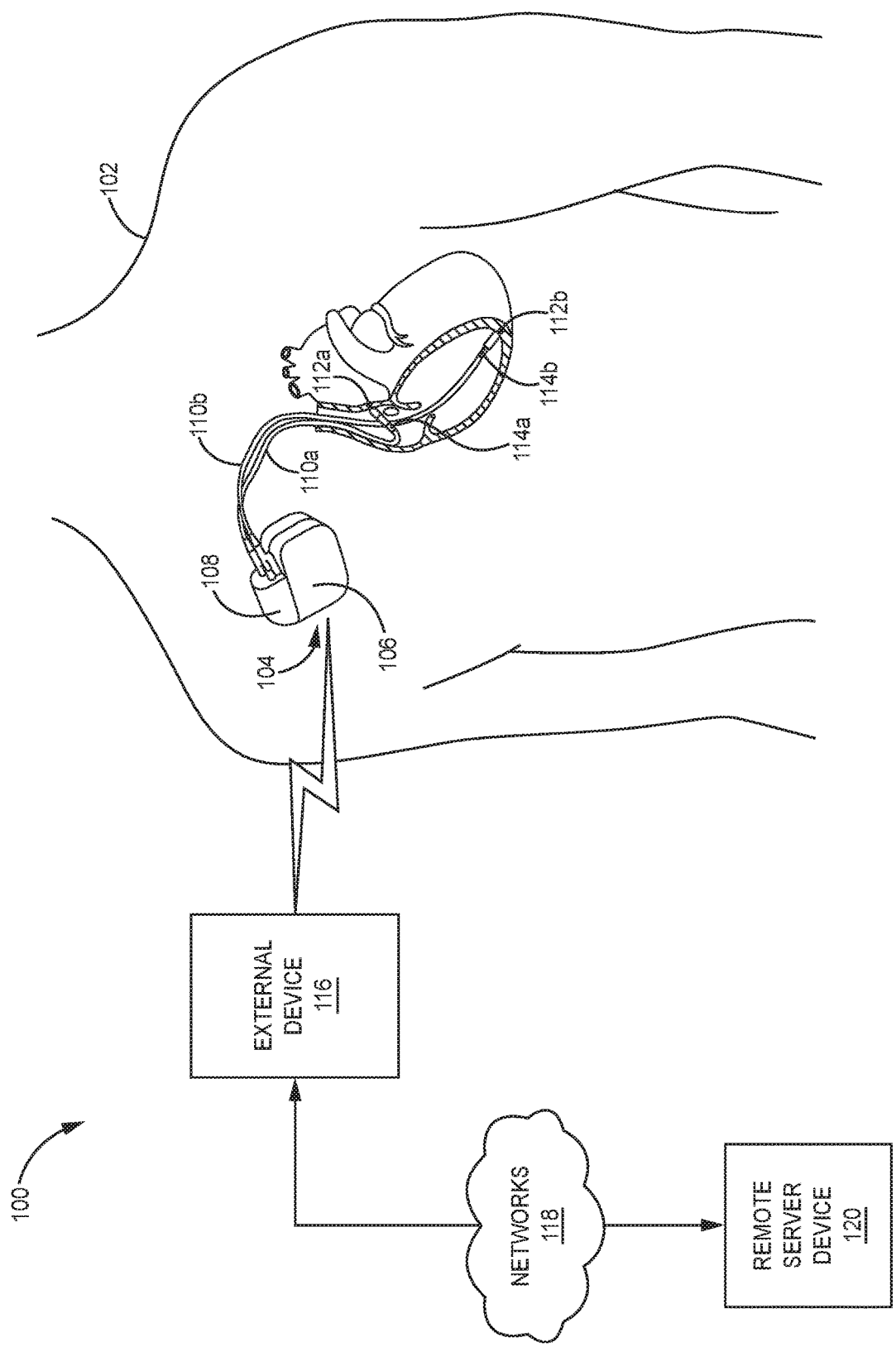
FIGS. 1, 2 and 3 illustrate schematic diagrams of example, non-limiting medical device telemetry systems configured to facilitate trusted pairing between an implantable device and an external device in accordance with one or more embodiments described herein.

With reference now to the drawings, FIG. 1 illustrates a schematic diagram of an example, non-limiting medical device telemetry system 100 configured to facilitate trusted pairing between an implantable device and an external device in accordance with one or more embodiments described herein. In the embodiment shown, medical device telemetry system 100 includes an implantable device 104 implanted within a body 102, an external device 116, one or more networks 118 and a remote server device 120. In some embodiments, the implantable device 104 is an IMD that is also configured to facilitate one or more diagnostic or treatment functions relative to the body 102. In other embodiments, the implantable device 104 is separate from an IMD (not shown in this embodiment) that is also implanted within the body 102 and communicatively and/or electrically coupled to the IMD.

Embodiments of devices, apparatus and systems herein can include one or more machine-executable components embodied within one or more machines (e.g., embodied in one or more computer-readable storage media associated with one or more machines). Such Components, when executed by the one or more machines (e.g., processors, computers, computing devices, virtual machines, etc.) can cause the one or more machines to perform the operations described.

One or more embodiments of medical device telemetry system 100 are described in connection with facilitating trusted pairing between the implantable device 104 and an external device, such as external device 116, in association with performing telemetry (i.e., wireless) communication between the implantable device 104 and the external device 116, and more particularly in association with performing telemetry communication using a non-proprietary telemetry communication technology/protocol. In telecommunication and computing in general, a "connection" is the successful completion of necessary arrangements so that two or more entities (e.g., devices, applications, users of the devices or application, etc.) can communicate. A "secure telemetry connection" is a connection that is encrypted by one or more security protocols to ensure the security of data flowing between two or more nodes.

Communication devices such as implantable device 104 and external device 116 have to agree on many physical layer and link layer aspects of the data to be exchanged before a successful connection can be established. Rules defining how to establish a connection and perform telemetry communications are referred to in wireless communication technology as "protocols." For example, in order to establish a secure telemetry connection, many communication protocols require a procedure called "pairing" wherein the respective devices form a trusted relationship prior to being able to communicate certain information with one another. Communication protocols cover authentication, error detection and correction, and signaling. Communications protocols are implemented in hardware and software. The term "non-proprietary telemetry communication technology/protocol" refers to any standardized telemetry communication technology/protocol that can be commercially used by more than one entity, either in an open source or licensed context. Many non-proprietary telemetry communication technologies/protocols have publically available specifications.

After the implantable device 104 and the external device 116 have paired and established a secure telemetry connection, in one or more embodiments, the implantable device 104 can use a non-proprietary telemetry protocol to exchange various types of information with external devices, including external device 116. For example, using a non-proprietary telemetry protocol, the implantable device 104 can transmit information to the external device 116. The information transmitted can include, but is not limited to, sensed physiological or biometric data from the body 102, diagnostic determinations made based on the sensed physiological or biometric data, therapy data associated with a therapy delivered to the body, and/or performance data regarding operation and performance of the implantable device 104 (e.g., power level information, information regarding strengths of signals received, information regarding frequency of received interrogation requests, remaining battery life, etc.). In some implementations, the implantable device 104 is an IMD configured to sense the physiological data or the biometric data from the body 102. The IMD can also provide therapy to the body 102 and retain the therapy information regarding the therapy that was provided. In other implementations, the implantable device 104 is associated with an implantable medical device configured to sense the physiological or biometric data or provide the therapy to the body 102.

In another example, the external device 116 can employ a non-proprietary telemetry communication to read data captured by the implantable device 104 (e.g., electrogram data or other physiological or biometric data sensed by the implantable device 104). In another example, using a non-proprietary telemetry protocol, the external device 116 can send information or signals to the implantable device 104 to program the implantable device 104 or to configure or re-configure the implantable device 104.

In some embodiments, the external device 116 can also provide information received from the implantable device 104 (and/or determinations or inferences made at the external device 116 based on the information) to a remote server device 120 via one or more wired and/or wireless networks 118. By way of example, but not limitation, the remote server device 120 can be associated with a networked medical monitoring service that is configured to remotely monitor information collected by implantable devices worn by patients (e.g., implantable device 104). The remote server device 120 can monitor and log the data, process the data and/or provide other users (e.g., medical caregiver personnel) access to the data via one or more networks 118. For example, the one or more networks 118 can include a cellular network, a wide area network (WAD, e.g., the Internet), a local area network (LAN), or a personal area network (PAN). For example, an external device 116 can communicate with the remote server device 120 (and vice versa) using virtually any desired wired or wireless technology, including, for example, cellular, WAN, wireless fidelity (Wi-Fi), Wi-Max, WLAN, and etc. In some embodiments, the remote server device 120 can also notify one or more user devices in response to reception of information that indicates a trigger event. For example, the remote server device 120 can notify a patient device (e.g., a device associated with the person wearing the implantable device 104) and/or the caregiver device in response to reception of physiological information indicating the patient's heart electrical activity is abnormal. In another example, the remote server device 120 can notify a patient device and/or the caregiver device in response to reception of information indicating telemetry connectivity between the implantable device 104 and the external device 116 is or may be compromised. In some embodiments, as described infra, the remote server device 120 can also facilitate trusted pairing between an external device (e.g., external device 116) and an implantable device (e.g., implantable device 104).

Information associated with the implantable device 104 can be provided to a wide variety of external devices. For example, the external device 116 can include but is not limited can include but is not limited to, a desktop computer, a laptop computer, a television, an Internet enabled television, a mobile phone, a smartphone, a tablet personal computer (PC), a personal digital assistant PDA, a heads-up display (HUD), virtual reality (VR) headset, augmented reality (AR) headset, or another type of wearable computing device. In some embodiments, the external device 116 includes a PC that is associated with the user wearing the implantable device 104. For example, the external device 116 can include a smartphone or other type of handheld or wearable device that is owned and operated by the patient wearing the implantable device 104. In another example, the external device 116 can include a PC that is operated by a medical caregiver of the patient, such as the patient's physician, nurse, at-home caregiver, mother, etc. In yet another example, the external device 116 can include a dedicated and/or stationary electronic computing device designed to remain at a home of the patient or at an office of a physician.

In various exemplary embodiments, the external device 116 includes an off-the-shelf device purchased at a store that can be configured to perform a variety of computing applications. These devices are configured to employ various types of non-proprietary telemetry protocols to communicate with other devices. For example, many modern mobile devices such as smart phones, tablet PCs and the like are configured to communicate using various non-proprietary telemetry protocols including but not limited to, BLUETOOTH®, BLUETOOTH® low energy (BLE), near field communication (NFC), Wireless Fidelity (Wi-Fi) protocol, Zigbee®, RF4CE, WirelessHART, 6LoWPAN, Z-Wave, ANT, and the like. In various embodiments, the implantable device 104 and/or the external device 116 can be configured to communicate using one or more non-proprietary telemetry protocols, including but not limited to the aforementioned non-proprietary telemetry communication protocols (e.g., BLUETOOTH®, BLE, etc.). In some embodiments, the implantable device 104 and/or the external device 116 can also be configured to communicate using one or more proprietary telemetry protocols.

As commercially available telemetry protocols are more frequently employed to conduct telemetry with an implantable device (e.g., implantable device 104), the knowledge of how to initiate a telemetry session with an implantable device 104 can become publicly available. As a result, an external device (e.g., external device 116) capable of employing the commercially available telemetry protocol (e.g., a smartphone, a tablet PC, and the like) may be able to initiate and possibly establish a telemetry connection with an implantable device (e.g., implantable device 104), even if the external device is not authorized to communicate with the implantable device.

For example, according to various non-proprietary telemetry protocols (e.g., BLUETOOTH®), in order to initiate a telemetry session with an implantable device (e.g., implantable device 104), an external device (e.g., external device 116) can send a connection request to the implantable device (e.g., implantable device 104) requesting to establish a telemetry connection with the implantable device. Upon reception of a connection request from an external device (e.g., external device 116), an initial telemetry connection can be established between the implantable device 104 and the external device 116. The implantable device 104 can then determine whether the external device 116 is authorized to communicate with the implantable device 104 prior to establishing a secure telemetry connection with the external device 116. In accordance with various non-proprietary telemetry communication protocols (e.g., BLUETOOTH®), in order to establish a secure telemetry connection between devices (e.g., between the implantable device 104 and the external device 116), the devices perform a pairing process that establishes a secure, trusted relationship between the devices. The pairing process is a mechanism where the parties involved in the communication exchange their identity information to establish trust and obtain the encryption information needed for the future data exchange. The secure, trusted relationship ensures that both devices have authorized telemetry communication between the respective devices and often involves a user/device authorization and/or identity verification procedure. After two devices have established a secure, trusted relationship (also referred to as becoming "paired"), the respective devices can communicate with one another without a subsequent authorization procedure. For example, in accordance with various embodiments, after the implantable device 104 has paired with an external device (e.g., external device 116), the external device can establish a secure telemetry connection with the implantable device 104 by sending a connection request with information that identifies the external device. The implantable device 104 can then accept the connection request based on a determination that the external device has been previously paired with the implantable device 104. The respective devices can further communicate data between one another using the encryption keys previously established between the devices in the pairing process.

The term "pairing" is generally associated with BLUETOOTH® technology, however, the concept of establishing a trusted, secured relationship using a pairing mechanism can be applied to other telemetry technologies. Depending on the user requirement and/or the capability of the device, BLUETOOTH® has several options for pairing. The BLUETOOTH® pairing process is typically triggered the first time a device (e.g., implantable device 104) receives a connection request from another device (e.g., external device 116) with which it is not yet paired. With the conventional BLUETOOTH® pairing process, security information is exchanged between the two devices (e.g., a unique code referred to a "passkey") to ensure that both users have agreed to pair with each other. Once the BLUETOOTH® pairing has occurred, data can be exchanged between the devices.

The pairing functionality that enables secure telemetry encryption between devices according to non-proprietary telemetry protocol is publically available via standards documents (e.g., BLUETOOTH® Specification Version 4.2 [Vol 1, Part A] 5.4.2 Key Generation, and BLUETOOTH®

Specification Version 4.2 [Vol 3, Part H] 3.6.1 Key Distribution and Generation). Accordingly, when the implantable device 104 employs a non-proprietary telemetry protocol to communicate with external devices, unauthorized third party devices can have the knowledge and ability to initiate pairing with the implantable device 104. In some scenarios, an unauthorized third party device may repeatedly initiate pairing with the implantable device 104, unintentionally or intentionally, thereby preventing the implantable device from performing useful communication with other devices and unnecessarily wasting power of the implantable device 104. In addition, some unauthorized third party devices may be able to successfully pair with the implantable device 104 depending on the level of security associated with the pairing protocol employed by the implantable device 104. As a result, unauthorized third party devices and/or users may be able to unlawfully communicate sensitive information with the implantable device 104. Further, in some scenarios, an external device paired with an implantable device may come into the hands of an unauthorized user, thereby making the implantable device 104 susceptible to the control of the unauthorized user.

In view of these compromising scenarios associated with usage of non-proprietary telemetry protocols, the subject disclosure provides various mechanisms to ensure trusted pairing between an implantable device (e.g., implantable device 104) and an external device (e.g., external device 116) in association with communication using a non-proprietary telemetry communication protocol. In one or more embodiments, the implantable device 104 and the external device 116 can be configured to initiate performance of a pairing procedure according to the standard protocol defined by the non-proprietary telemetry communication protocol used by the respective devices to communicate. For example, in an embodiment in which the respective devices are configured to communicate using a BLUETOOTH® protocol (e.g., BLE) or the like, the implantable device 104 can be configured to respond to a connection request received from an unpaired external device (e.g., external device 116) by initiating the pairing procedure according to the standard specification defined by the BLUETOOTH® protocol. In some implementations, the connection request sent from the external device 116 to the implantable device 104 can be characterized and interpreted by the implantable device 104 as a "pairing request." For example, the connection request can include information and/or formatting that indicate the specific type of connection request is a "pairing request." In other implementations, the implantable device 104 can be configured to automatically interpret connection requests received from external devices that the implantable device has not previously been paired with as pairing requests and automatically initiate the pairing procedure according to the defined non-proprietary telemetry protocol.

Regardless of the specific non-proprietary telemetry communication protocol employed by the implantable device 104 and the external device 116, the standard pairing procedure generally involves generating and exchanging security information that will be used by the respective devices to establish a secure telemetry connection. For example, the implantable device 104 and the external device 116 can generate or determine one or more encryption keys to be used by the respective devices for data encryption/decryption in subsequent communications. The respective devices can also exchange identification information that respectively identifies the respective devices. For example, the implantable device 104 can provide the external device 116 with a unique identifier for the implantable device 104 and the external device 116 can provide the implantable device 104 with a unique identifier for the external device. For instance the unique identifier for the implantable device 104 could include but is not limited to, a serial number, a universally unique identifier (UUID), a model number, an account number, a username, or the like. Similarly, the unique identifier for the external device 116 can include but is not limited to, a UUID, a serial number, a model number, a phone number, a mobile subscriber identification number (MSIN), an international mobile subscriber identity (IMSI) number, an account number, a username, or the like.

Depending on the particular non-proprietary telemetry communication protocol employed, the pairing procedure can involve one or more additional known (e.g., publically available via the protocol specification) measures to establish a trusted relationship between the respective devices. For example, the BLE pairing process between two devices can involve the exchange of pairing information, authentication of the link, and distribution of the keys. The exchange of pairing information between the two devices can be done through the pairing request (e.g., which can be transmitted by the external device 116 in accordance with the subject disclosure), and the pairing response Security Manager Protocol (SMP) messages (e.g., which can be transmitted by the implantable device 104 in accordance with the subject disclosure). The authentication step of the BLE the pairing procedure can be performed based on the information exchanged in the previous step in the SMP pairing request and pairing response messages. In this step, a temporary key (TK) is generated followed by generation of a short term key (STK). The third phase of the BLE pairing procedure is the distribution of the keys. The keys are distributed using specific SMP packets. The keys are encrypted with the STK and once stored in a security database must have the same properties. Only the security information specified in the pairing request and response is distributed. Additional details regarding the BLE pairing procedure can be found in the BLUETOOTH SPECIFICATION Version 4.2 [Vol 1, Part A] 5.4.2 Key Generation, and the BLUETOOTH SPECIFICATION Version 4.2 [Vol 3, Part H] 3.6.1 Key Distribution and Generation.

In addition to the known or standard pairing procedures associated with the non-proprietary telemetry communication protocol employed by the implantable device 104 and the external device 116, the subject disclosure provides one or more additional techniques to preclude unauthorized external devices from pairing with the implantable device 104. In some embodiments, the subject disclosure also provides techniques to minimize the ability for unauthorized external devices to repeatedly attempt to pair with the implantable device 104.

In particular, in accordance with various embodiments, in order to pair with an external device or otherwise establish a trusted relationship with the external device (e.g., external device 116), the implantable device 104 can be configured to employ a validation procedure that is supplementary to the standard pairing procedure defined by the non-proprietary telemetry protocol employed by the implantable device 104 to communicate with the external device 116 (e.g., BLE). The supplementary validation procedure is not defined by or included in the pairing procedure defined by the non-proprietary telemetry protocol employed by the implantable device 104 to communicate with the external device 116 (e.g., the supplementary validation procedure is not defined in the BLE specification or otherwise publically available). Accordingly, only authorized external devices that are configured to comply with the supplementary validation protocol will be able to successfully pair with the implantable device 104. In addition, even if the supplementary validation procedure is learned by an unauthorized external device, the auxiliary validation procedure can require one or more heightened security measures that make it very difficult if not impossible for unauthorized external devices to perform or bypass.

The subject techniques can be employed in association with pairing specific external devices with implantable devices and/or specific user identities with implantable devices. These user identities can be represented by user accounts. For example, in some implementations, using a dedicated application or program on an external device 116 that is configured to facilitate communicating with one or more implantable devices, a user can establish a user account. This dedicated application or program is referred to herein as an "implantable device application" (e.g., implantable device application 902 described in greater detail infra with reference to FIG. 9). The user account can further become paired with one or more implantable devices in accordance with the subject trusted pairing techniques. According to these embodiments, a single external device can be associated with several different user accounts. In order for a particular user to be able to employ the external device 116 to perform secure telemetry communications with the implantable device 104, the particular user account associated with the user will need to be paired with the implantable device 104 and the telemetry connection between the external device 116 and the implantable device 104 will need to be associated with the particular user account. According, in one or more embodiments, the implantable device 104 can pair or otherwise established a trusted telemetry relationship with a particular external device, a particular user account/identity and/or a particular external device and user account combination.

In accordance with various embodiments, after the implantable device 104 and an external device (e.g., external device 116) and/or a specific user account (that represents a specific user identity) have initiated a pairing procedure, the implantable device 104 can be configured to prevent pairing between the implantable device 104 and the external device and/or user account unless a defined validation event occurs. In some embodiments, the validation event can involve the timely provision, by the external device 116 to the implantable device 104, of validation information. For example, in some implementations the validation information can include but is not limited to, a defined validation command, a defined key, a defined code, a defined password, a unique signal, and the like. The external device 116 can be configured to provide the validation information to the implantable device 104 via signaling message (e.g., an SMP message) associated with the non-proprietary telemetry communication protocol used to initiate pairing with the implantable device (e.g., BLE). In other embodiments, the external device 116 can be configured to provide the validation information to the implantable device 104 using a different telemetry communication protocol relative to the non-proprietary telemetry communication protocol used to initiate the paring procedure. For example, the external device 116 can be configured to provide the validation information using an out-of-band signal, an NFC signal, a proprietary telemetry communication signal, an inductive communication signal, or the like. Still in other embodiments, the validation information can be in the form of a unique signal provided by the external device 116 to the implantable device 104 that in and of itself represents a validation command. For example, the unique signal can include a unique out-of-band signal, a unique NFC signal, a unique proprietary radio frequency (RF) telemetry communication signal, a unique optical signal, a unique audio signal, a unique vibration signal, a unique electromagnetic induction signal, or the like.

Regardless of the manner in which the validation information is conveyed to the implantable device 104, the implantable device 104 can be configured to interpret the validation information as indication that the external device and/or a particular user account is authorized to pair with the implantable device 104. Accordingly, based on reception of the validation information, the implantable device 104 can pair with the external device and/or the user account or otherwise establish a trusted relationship with the external device and/or the user account. Once the implantable device 104 has paired with the external device or otherwise established a trusted relationship with the external device, the implantable device can authorize and establish telemetry connections or sessions with the external device without requiring the external device to perform another pairing or validation procedure. The implantable device 104 can further be configured to allow communication of various types of data (e.g., sensitive data) between the external device 116 and the implantable device 104, not simply control data or data otherwise used merely to set up a telemetry connection. For example, via an established telemetry connection, the implantable device 104 can allow communication of application data packets in addition to control data packets.

In some embodiments, in order for the external device 116 to be able to provide the validation information to the implantable device 104 and/or in order for the implantable device 104 to accept the validation information, the implantable device 104 and the external device 116 must also share a common encryption key, referred to herein as a host key. In one implementation, the external device 116 can learn the host key via an asymmetric-cryptography scheme (or public-key scheme). In another implementation, the host key can be programmed into the implantable device 104 by an authorized external device (e.g., at manufacturing, prior to implantation of the implantable device 104 into patient, or after implantation). Information defining the host key associated with the implantable device 104 can further be stored at a secure source (e.g., at the remote server device 120) and received by the external device 116 from the secure source based on performance of some type of authentication/authorization procedure. In some implementations, the external device 116 and the implantable device 104 can discover the respective devices share the host key in association with initiation of the pairing process. According to this implementation, the implantable device 104 can be configured to authorize proceeding with the pairing process based on reception of the correct host key from the external device 116. For example, based on reception of the correct host key, the implantable device 104 and the external device 116 can negotiate the encryption keys to be used when communicating using BLE after pairing is complete. In another example implementation, the external device 116 can provide the host key to the implantable device in association with the validation information. According to this implementation, the implantable device can reject the validation information unless is it received with the valid host key.

In one implementation, the validation information can indicate that a remote server verified the external device and/or user account (that represents the specific entity operating the external device) as being authorized to pair with the implantable device 104. For example, with respect to medical device telemetry system 100, the external device 116 or a user account associated with the external device 116, can be configured to perform an authorization procedure with the remote server device 120. It is understood that an "authorization procedure" can include, but is not limited to, authorization operations and communication, specific authentication operations and communications, and the like. The authorization procedure can ensure that the external device and/or a specific user of the external device is authorized to pair with the implantable device 104. Based on the authorization procedure, the remote server device 120 can provide the external device 116, and/or the external device 116 can generate, unique validation information (e.g., a pass-code, a password, a secret key, etc.) that indicates the external device 116 and/or the account associated with the external device is authorized to pair with the implantable device 104.

For example, the remote server device 120 can maintain information that identifies implantable devices (e.g., 104) and associates information with the respective implantable devices that identifies what external devices are authorized to pair with the respective implantable devices. In some implementations, the respective implantable devices can be associated with one or more user accounts that identify one or more specific entities (e.g., users) that are authorized to use an external device to communicate with the implantable device. In association with a pairing procedure or prior to the pairing procedure, in one implementation, the external device 116 and/or a user (e.g., as identified by a specific user account) of the external device 116 can send a request to the remote server device 120 requesting the verification information necessary to pair with an implantable device (e.g., implantable device 104). The request can also identify the particular implantable device with which the external device 116 and/or user desires to pair. Based on reception of the request, the remote server device 120 can perform an authorization procedure that involves receiving verification information (e.g., a username and password or another type of security information) from the external device that verifies the identity of the external device 116 and/or the user or user account. The remote server device 120 can compare the verification information to the stored information associated with the external device to determine whether the external device 116 and/or the user account is authorized to pair with the implantable device. Based on a determination that the external device 116 and/or the user account is authorized, in one embodiment the remote server device 120 can provide the external device 116 and/or user account with the validation information. For example, in some embodiments, the remote server device 120 can provide the external device 116 with the validation information in the form of a unique code, password, key, etc., that indicates the external device 116 is authorized to pair with the implantable device 104. The external device 116 and/or user account associated with the external device can further be configured to provide the unique code, password, key, etc., to the implantable device 104 in association with a pairing request. In another embodiment, based on a determination that the external device 116 and/or the user account is authorized, in one embodiment the remote server device 120 can provide the external device 116 with information authorizing and/or instructing the external device 116 to generate a unique signal that represents a validation command. The information defining how to generate the unique signal can be included in the instruction sent be the remote server device 120 to the external device or retained in memory of the external device 116 (e.g., that is accessible by the implantable device application). In one or more implementations, the unique signal can include a signal generated using a different communication protocol relative to the non-proprietary telemetry communication protocol employed by the external device 116 to initiate the pairing. For example, the unique signal can include an NFC signal, an out-of-band signal, a proprietary telemetry signal or the like. In another example, the unique signal can include a wireless signal that is not a frequency (RF) signal. For example, the unique signal can be an electromagnetic induction signal, an audio signal, an optical signal, a vibration signal, and the like.

In other embodiments, rather than communicating with a remote server device 120 in association with performing an authorization procedure to obtain or generate the validation information, the external device 116 be configured to perform an authorization procedure without communicating with a remote server device (e.g., using an implantable device application). According to these embodiments, the remote server device 120 can be removed from the medical device telemetry system 100, as shown in FIG. 2.

Figure 2:
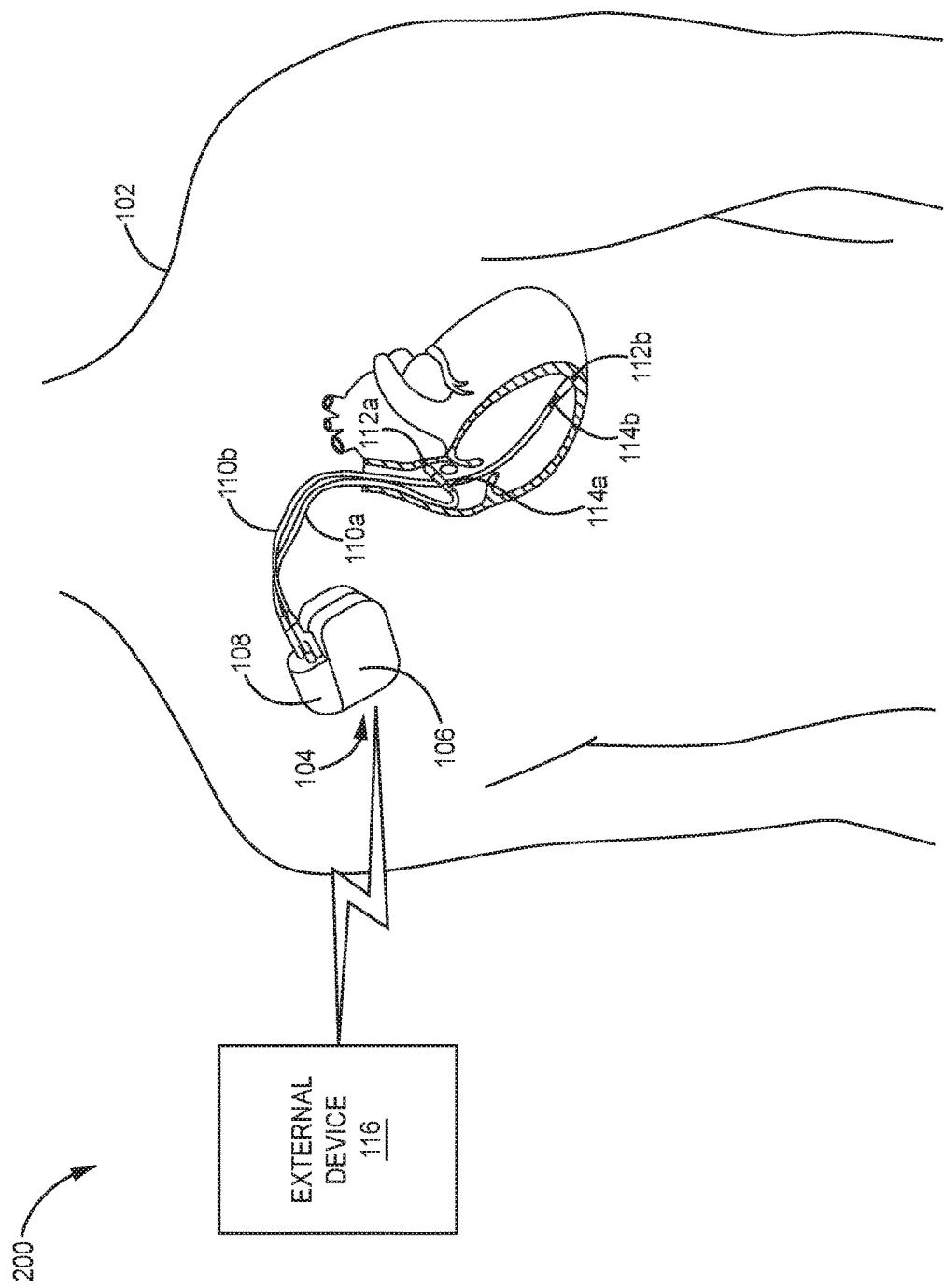

FIG. 2 illustrates a schematic diagram of another example, non-limiting medical device telemetry system 200 configured to facilitate trusted pairing between an implantable device and an external device in accordance with one or more embodiments described herein. Repetitive description of like elements employed in respective embodiments is omitted for sake of brevity. In accordance with medical device telemetry system 200, the external device 116 can include an implantable device application that facilitates performing telemetry communications with an implantable device (e.g., implantable device 104) using a non-proprietary telemetry communication protocol (e.g., BLE). The implantable device application can further be configured to generate the validation information based on performance of an authorization procedure that verifies the external device 116 and/or a user of the external device 116 is authorized to pair with the implantable device 104. In one or more implementations, the authorization procedure can require user input to the external device 116 of a unique code, password, signal etc. The unique code, password, signal, etc., can be associated with information accessible (e.g., in memory of the external device 116) to the implantable device application that indicates the entity that provided the input is authorized to pair with the implantable device 104. Based on reception of the unique code, password, signal, etc., from the user in association with the authentication/authorization procedure, the implantable device application can be configured to generate the validation information or access previously generated validation information and provide the validation information to the implantable device 104.

For example, in one implementation, a user of the external device 116 can open the implantable device application of the external device and send a pairing request to the implantable device 104. Based on sending the pairing request, the implantable device application can generate a prompt that requests the user provide input (e.g., a username or password, a pass-code, a secret key, etc.) that verifies the user identity and/or verifies that the user is authorized to pair with the implantable device 104. The implantable device application can further have access to information stored in memory of the external device 116 that associates the required user input with an authorization to pair with the implantable device 104. Based on reception of the user correct input, in one implementation the implantable device application can then generate and/or otherwise provide the validation information to the implantable device 104. For example, in implementations in which the validation information is in the form of a unique code, password key, symbol, etc., the implantable device application can be configured to provide the validation information to the implantable device 104 to facilitate completion of the pairing procedure. In another implementation, in which the validation information is in the form of a unique signal (e.g., an RF signal or a non-RF signal), the external device can be configured to generate and send the unique signal to the implantable device 104.

In another example implementation, in order to initiate communication with the implantable device 104 using an external device, a user of the external device 116 can be required to employ a dedicated implantable device application. Further, in order to employ the implantable device application, the user can be required to have a registered account with the implantable device application, and in order to access the user account, the implantable device application can require the user provide input (e.g., username or password, a pass-code, etc.) that verifies the identity of the user as associated with a user account. Once the user has access to his or her account based on provision of the input (e.g., username or password, etc.), the user can further have access to the validation information (e.g., stored in memory of the external device 116) needed to complete a pairing with an implantable device. For example, in one embodiment, the implantable device application can be configured to automatically access, generate, and/or provide defined validation information to the implantable device in association with a pairing request based on the user being logged into his or her account. In another example, based on the user being logged in to his or her account, the implantable device application can provide the user access to previously defined validation information. According to this example, when prompted in association with a pairing request, the user can access the validation information and direct the implantable device application to provide it to the implantable device 104.

It should be appreciated that the type of user input needed to access the validation information or otherwise cause the implantable device application to generate and/or provide the validation information can vary depending on the features and functionalities of the external device 116. For example, in some implementations, rather than providing a secret code, password, etc., the user input can include biometric information (e.g., a fingerprint). In another implementation, the user input can include a signal provided by an additional verification device (not shown). For example, an additional verification device can be configured to communicate a secret code or password to the external device 116 via NFC, a RFID tag that can be read by the external device 116, or another proprietary or non-proprietary close range communication protocol. This secret code or password can serve as the input necessary for generating the validation information by the implantable device application of the external device 116.

Figure 3:
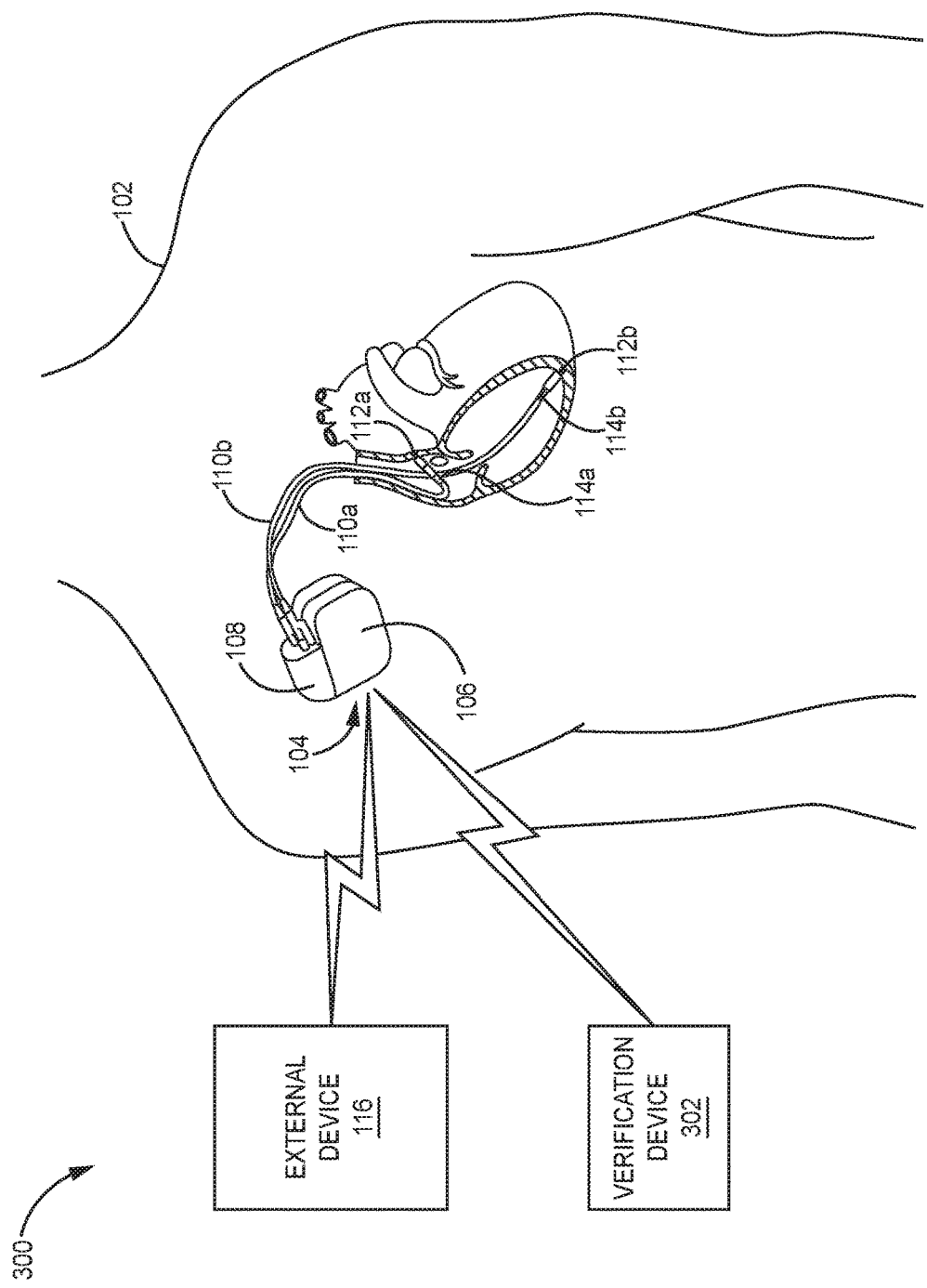

Still in other embodiments, rather than having the external device 116 provide validation information to the implantable device 104, the validation event can involve provision of the validation information by an additional verification device. For example, FIG. 3 illustrates a schematic diagram of another example, non-limiting medical device telemetry system 300 configured to facilitate trusted pairing between an implantable device and an external device in accordance with one or more embodiments described herein. Medical device telemetry system 300 includes similar features and functionalities as medical device telemetry system 200 with the addition of verification device 302. Repetitive description of like elements employed in respective embodiments is omitted for sake of brevity.

In accordance with medical device telemetry system 300, the external device 116 (and/or a particular user account associated with the external device 116) can initiate pairing with the implantable device 104 in accordance with the non-proprietary telemetry protocol employed by the respective devices (e.g., BLE). However, in order to become effectively paired with the implantable device 104, the verification device 302 can be required to provide the validation information to the implantable device 104 using a close range wireless communication protocol/technology that requires the verification device 302 to be within close proximity (e.g., a few meters or less) of the implantable device 104. For example, the close range communication protocol/technology can include an RF protocol such as BLUETOOTH®, NFC or the like. In other embodiments, the verification device 302 can be configured to provide the validation information in the form of a command communicated to the implantable device using a unique non RF signal (e.g., an optical signal, an audio signal, an electromagnetic induction signal, a vibration signal, etc.). The verification device 302 can include a device that is only intended to be operated by one or more users with explicit authority to authorize pairing between a particular external device/user account and the implantable device 104 (e.g., the patient wearing the implantable device 104, the patient's caregiver, the patient's doctor, and the like). In accordance with medical device telemetry system 300, the user that operates the verification device 302 can be the same user that operates the external device 116 or another user (e.g., the patient's doctor, the patient's caregiver, etc) that cooperates with the user operating the external device 116 to facilitate pairing the external device 116 with the implantable device 104. As a result, an external device alone will not be able to successfully pair with the implantable device 104.

For example, in accordance with one or more embodiments of medical device telemetry system 300, using an implantable device application of the external device 116 that is configured to facilitate communicating with implantable devices, a first user operating the external device 116 can initiate the standard pairing procedure between the external device 116 and the implantable device (e.g., using BLE). In association with the pairing procedure, the implantable device application can generate a prompt that requests the verification device 302 provide the validation information to the implantable device 104. The first user operating the external device 116, or a second user cooperating with the first user, can use the verification device 302 to provide the implantable device 104 with the validation information. For example, the first or second user can bring the verification device within transmission rage of the implantable device, and press a button the verification device 302 or otherwise cause the verification device 302 to provide the implantable device 104 with the validation information. Upon reception of the validation information, the implantable device 104 and the external device 116 can complete the pairing procedure can become successfully paired. Additional details of example embodiments of the subject techniques for facilitating trusted pairing between an implantable device (e.g., implantable device 104) and an external device (e.g., external device 116) are discussed below with respect to FIGS. 4-12.

It is to be appreciated that the implantable device 104 can include one or more devices, transducers and/or circuits that can facilitate telemetry communication and disablement of telemetry communication. For example, the implantable device 104 can include a transmitter that transforms electrical power into a signal associated with transmitted data packets. Additionally, the implantable device 104 can include one or more devices, transducers and/or circuits that can facilitate receiving information from one or more devices (e.g., the external device 116, a server, etc.). For example, the implantable device 104 can include a receiver that transforms a signal into electrical power.

In the example shown in medical device telemetry system 100, a person operating the external device 116 is a patient in which the implantable device 104 is implanted. In another example, another person (e.g., such as medical caregiver) interacting with the patient in which the implantable device 104 is implanted can operate the external device 116 outside the body 102 in which the implantable device 104 is located. In various embodiments, the implantable device 104 can include any number of different types of implantable devices configured to communicate with the external device 116 or another external device. The particular, size, shape, placement and/or function of the implantable device 104 may not be critical to the subject disclosure in some embodiments.

In one embodiment, as mentioned, the implantable device 104 is or includes an IMD. For example, some example IMDs can include, but are not limited to, cardiac pacemakers, cardiac defibrillators, cardiac re-synchronization devices, cardiac monitoring devices, cardiac pressure monitoring devices, spinal stimulation devices, neural stimulation devices, gastric stimulation devices, diabetes pumps, drug delivery devices, and/or any other medical devices. In various embodiments, however, the implantable device 104 can be or include any number of other types of implantable devices that are not IMDs.

For exemplary purposes, the implantable device 104 is illustrated in medical device telemetry system 100 as an IMD implanted within the chest of a patient and configured to provide medical treatment or therapy associated with a heart disease or condition (e.g., an implantable cardioverter-defibrillator (ICD) and/or a pacemaker). In addition to the medical treatment, the implantable device 104 can also be configured to provide the data packetizing and communication operations described herein. The implantable device 104 includes a housing 106 within which electrical components and one or more power sources are housed. The electrical components can be powered via the one or more power sources. A power source (not shown) can include, but is not limited to, a battery, a capacitor, a charge pump, a mechanically derived power source (e.g., microelectromechanical systems (MEMs) device), or an induction component. The various embodiments described herein can provide improved management of power associated with the one or more power sources.

The electrical components can vary depending on the particular features and functionality of the implantable device 104. In various embodiments, these electrical components can include, but are not limited to, one or more processors, memories, transmitters, receivers, transceivers, sensors, sensing circuitry, therapy circuitry, antennas and other components. In an embodiment, the electrical components can be formed on or within a substrate that is placed inside the housing 106. The housing 106 can be formed from conductive materials, non-conductive materials or a combination thereof. For example, housing 106 can include a conductive material, such as metal or metal alloy, a non-conductive material such as glass, plastic, ceramic, etc., or a combination of conductive and non-conductive materials. In some embodiments, the housing 106 can be a biocompatible housing (e.g., a liquid crystal polymer, etc.).

In the embodiment shown, the implantable device 104 is also an IMD and further includes leads 110a,b connected to the housing 106. The leads 110a,b extend into the heart and respectively include one or more electrodes. For example, as depicted in medical device telemetry system 100, leads 110a,b each include a respective tip electrodes 112a,b and ring electrodes 114a,b located near a distal end of their respective leads 110a,b. When implanted, tip electrodes 112a,b and/or ring electrodes 114a,b are placed relative to or in a selected tissue, muscle, nerve or other location within the body 102 of the patient. As depicted in medical device telemetry system 100, tip electrodes 112a,b are extendable helically shaped electrodes to facilitate fixation of the distal end of leads 110a,b to the target location within the body 102 of the patient. In this manner, tip electrodes 112a,b are formed to define a fixation mechanism. In other embodiments, one or both of tip electrodes 112a,b may be formed to define fixation mechanisms of other structures. In other instances, leads 110a,b may include a fixation mechanism separate from tip electrodes 112a,b. Fixation mechanisms can be any appropriate type, including a grapple mechanism, a helical or screw mechanism, a drug-coated connection mechanism in which the drug serves to reduce infection and/or swelling of the tissue, or other attachment mechanism.

Leads 110a,b are connected at a proximal end of the implantable device 104 via connector block 108. Connector block 108 may include one or more receptacles that interconnect with one or more connector terminals located on the proximal end of leads 110a,b. Leads 110a,b are ultimately electrically connected to one or more of the electrical components within housing 106. One or more conductors (not shown) extend within leads 110a,b from connector block 108 along the length of the lead to engage the ring electrodes 114a,b and tip electrodes 112a,b, respectively. In this manner, each of tip electrodes 112a,b and ring electrodes 114a,b is electrically coupled to a respective conductor within its associated lead bodies. For example, a first electrical conductor can extend along the length of the body of lead 110a from connector block 108 and electrically couple to tip electrode 112a and a second electrical conductor can extend along the length of the body of lead 110a from connector block 108 and electrically couple to ring electrode 114a. The respective conductors may electrically couple to circuitry, such as a therapy module or a sensing module, of the implantable device 104 via connections in connector block 108. In one or more embodiments, the implantable device 104 is configured to deliver therapy to the heart (or other location) via the electrical conductors to one or more of electrodes 112a and 112b and 114a and 114b. In the case of pacing therapy, for example, therapy circuitry within the implantable device 104 can generate and deliver pacing pulses via a unipolar electrode configuration, e.g., using electrodes 112a and 112b and a housing electrode of the implantable device 104. In other instances, the therapy circuitry within the implantable device 104 can deliver pacing pulses via a bipolar electrode configuration, e.g., using electrodes 112a and 112b and ring electrodes 114a and 114b. The therapy circuitry may include one or more pulse generators, capacitors, and/or other components capable of generating and/or storing energy to deliver as pacing therapy in accordance with a pacing regime stored within memory.

Implantable device 104 can also receive sensed electrical signals on the electrical conductors from one or more of electrodes 112a and 112b and 114a and 114b. The implantable device 104 can sense the electrical signals using either a unipolar or bipolar electrode configuration. Sensing circuitry of the implantable device 104 may process the sensed electrical signals and the implantable device 104 may analyze the processed and/or or sensed electrical signals and provide the pacing as a function of the sensed electrical signal. The sensing circuitry may include one or more sense amplifiers, filters, rectifiers, threshold detectors, comparators, analog-to-digital converters (ADCs), or other analog or digital components.

The configuration, features and functionality of implantable device 104 are merely provided as an example. In other examples, the implantable device 104 can include more or fewer leads extending from the housing 106. For example, the implantable device 104 can be coupled to three leads, e.g., a third lead implanted within a left ventricle of the heart of the patient. In another example, the implantable device 104 can be coupled to a single lead that is implanted within the ventricle of the heart of the patient. In other embodiments, the lead may be an extravascular lead with the electrodes implanted subcutaneously above the ribcage/sternum or substernally underneath or below the sternum. Example extravascular ICDs having subcutaneous electrodes are described in U.S. Patent Publication No. 2014/0214104 (now U.S. Pat. No. 9,072,914) (Greenhut et al.) and U.S. Patent Publication No. 2015/0133951 (Seifert et al.), each of which is incorporated herein in its entirety. One example extravascular ICD having substernal electrodes is described in U.S. Patent Publication No. 2014/0330327 (Thompson-Nauman et al.). In some embodiments, the implantable device 104 can include other leads (e.g., atrial lead and/or left ventricular lead). As such, implantable device 104 can be used for single chamber or multi-chamber cardiac rhythm management therapy. In addition to more or fewer leads, each of the leads may include more or fewer electrodes. In instances in which the implantable device 104 is used for therapy other than pacing (e.g., defibrillation or cardioversion), the leads can include elongated electrodes, which may, in some instances take the form of a coil. The therapy circuitry of the implantable device 104 can generate and deliver defibrillation or cardioversion shocks to the heart via any combination of the elongated electrodes and housing electrode. The therapy circuitry may include one or more high voltage (HV) output capacitors and a HV charging circuit, which may include one or more capacitors, resistors, inductors, transformers, switches, or other analog or digital components, and discharging circuitry to deliver cardioversion or defibrillation therapy, including, for example, an H-bridge circuit. In another embodiment, the implantable device 104 can include leads with a plurality of ring electrodes (e.g., as used in some implantable neurostimulators), without a tip electrode or with one of the ring electrodes functioning as the "tip electrode."

In another embodiment, the implantable device 104 may include no leads, as in the case of an intracardiac pacemaker, implantable cardiac monitor or a leadless pressure sensor. In the case of an intracardiac pacemaker, the device may include a housing sized to fit wholly within the patient's heart. In one example, the housing may have a volume that is less than 1.5 cc and, more preferably, less than 1.0 cubic centimeter (cc). However, the housing may be greater than or equal to 1.5 cc in other examples. The intracardiac pacemaker includes at least two electrodes spaced apart along the outer portion of the housing for sensing cardiac electrogram signals and/or delivering pacing pulses. Example intracardiac pacemakers are described in commonly-assigned U.S. Patent Publication No. 2012/0172690 (Anderson et al.), U.S. Patent Publication No. 2012/0172941 (now U.S. Pat. No. 8,386,051) (Kenneth), and U.S. Patent Publication No. 2014/0214104 (now U.S. Pat. No. 9,072,914) (Greenhut et al.), each of which is incorporated herein in its entirety. In the case of a leadless pressure sensor, the device can include a housing having a fixation member and a pressure sensing component. One example of a leadless pressure sensor is described in U.S. Patent Publication No. 2012/0108922 (now U.S. Pat. No. 8,475,372) (Schell et al.), which is incorporated herein in its entirety.

In yet another embodiment, the implantable device 104 may be a non-cardiac device. Example non-cardiac devices may include, but are not limited to, neurostimulation devices and drug pump devices. Neurostimulation devices may be used to stimulate targets that include, but are not limited to, spinal cord targets, deep brain stimulation (DBS) targets, gastric nerves, pelvic nerves, peripheral nerves, and/or a variety of organs, such as the stomach, bladder, or the like. Example drug pump devices may be configured to deliver medication for treatment of chronic pain or diabetes.

Figure 4:
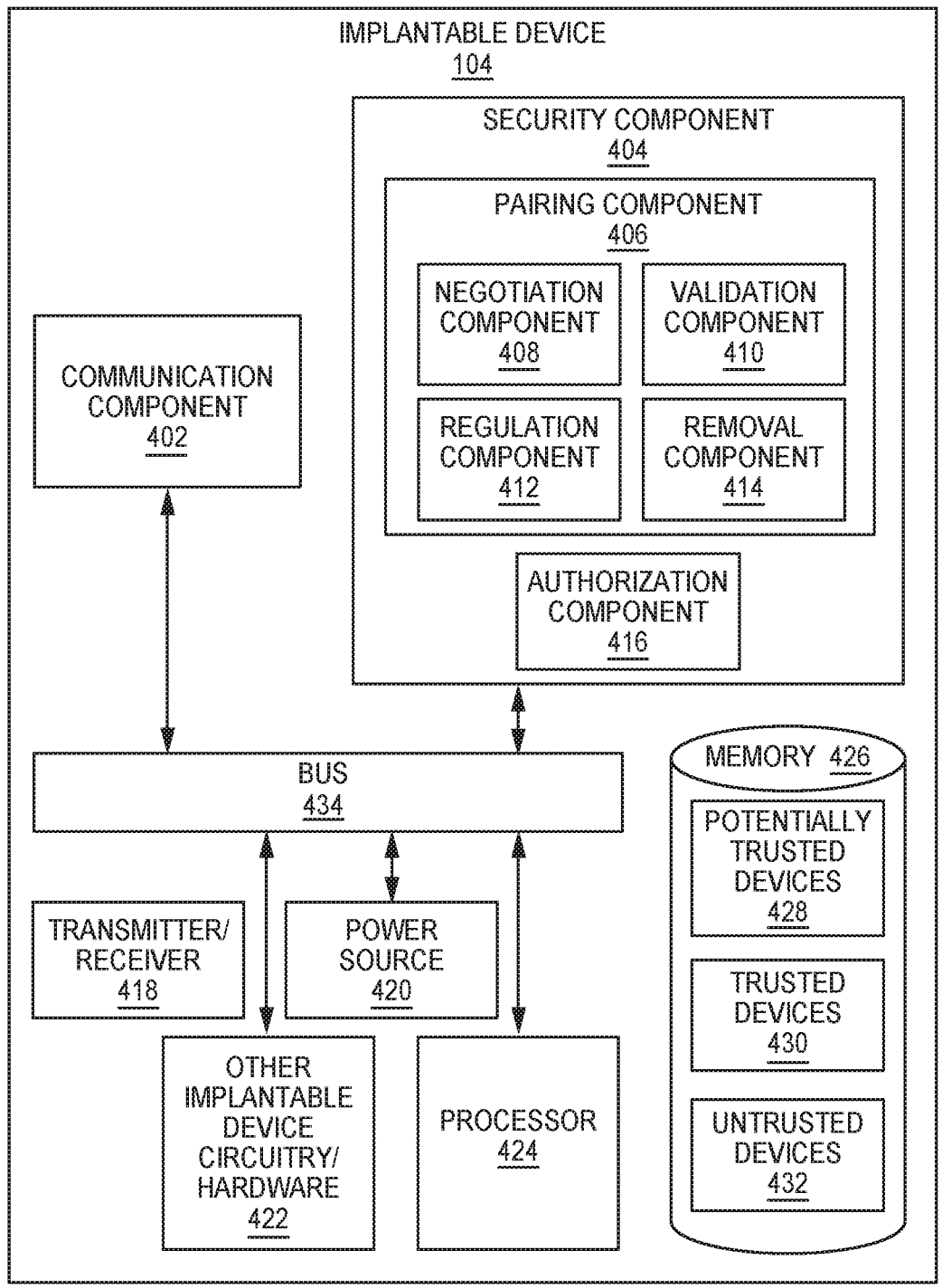
FIG. 4 illustrates a block diagram of an example, non-limiting implantable device in accordance with one or more embodiments described herein.

FIG. 4 illustrates a block diagram of an example, non-limiting implantable device (e.g., implantable device 104) in accordance with one or more embodiments described herein. The implantable device 104 can include a communication component 402 and a security component 404 respectively configured to facilitate trusted pairing between the implantable device 104 and one or more external devices (e.g., external device 116) in association with usage of a non-proprietary telemetry communication protocol to communicate with the one or more external devices. The implantable device 104 can also includes a transmitter/receiver 418 (or transceiver), a power source 420, and other implantable device circuitry/hardware 422.

Various aspects of the device, systems, apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. Accordingly, in one or more embodiments, the implantable device 104 can include memory 426 configured to store computer executable components and instructions (e.g., communication component 402 and security component 404). The implantable device 104 can also include a processor 424 to facilitate operation of the instructions (e.g., computer executable components and instructions) by the implantable device 104. Implantable device 104 can include a bus 434 that couples the various components of the implantable device 104, including, but not limited to, the communication component 402, the security component 404, the transmitter/receiver 418, the power source 420, the other implantable device circuitry/hardware 422, the processor 424 and the memory 426. Repetitive description of like elements employed in other embodiments described herein is omitted for sake of brevity.

With reference to FIGS. 1, 2, 3 and 4, the communication component 402 is configured to facilitate telemetry communication between implantable device 104 and one or more external devices (e.g., external device 116, verification device 302, and the like). For example, the communication component 402 can be configured to control operation of the transmitter/receiver 418 (or transceiver) to facilitate establishing a telemetry connection with external device 116 and control transmission and reception of data packets by the implantable device 104. The type of the transmitter/receiver 418 can vary depending on the type of telemetry protocol the implantable device 104 is configured to employ. In some embodiments, the transmitter/receiver 418 can be configured to perform different types of telemetry protocols. In other embodiments, the implantable device 104 can include a plurality of different transmitters/receivers that are respectively configured to perform different types of telemetry communication protocols. In some embodiments, rather than including a transmitter and a receiver that do not share common circuitry, the implantable device 104 can include a transceiver.

The communication component 402 can be configured to facilitate telemetry communication between the implantable device 104 and an external device (e.g., external device 116) using a variety of telemetry communication protocols including proprietary and non-proprietary telemetry protocols. For example, in one or more embodiments, communication component 402 can communicate with external device 116 using NFC, or another type of communication protocol over a PAN or a LAN (e.g., a Wi-Fi network) that can provide for communication over greater distances than NFC protocol or that can provide various advantages (such as increased security).

In some embodiments, the communication component 402 can control transmission and reception of data packets via a communication channel associated with a communication protocol utilizing lower energy consumption than a conventional communication protocol for wirelessly transmitting data. For example, in a non-limiting example, communication component 402 controls transmission and reception of data packets using BLE protocol. Other communication protocols that can be employed by communication component 402 to communicate with external device 116 can include, but are not limited to, other BLUETOOTH® communication protocols, a Session Initiation Protocol (SIP) based protocol, a Zigbee® protocol, a RF4CE protocol, a WirelessHART protocol, a 6LoWPAN (IPv6 over Low power Wireless Personal Area Networks) protocol, a Z-Wave protocol, an ANT protocol, an ultra-wideband (UWB) standard protocol, a radio frequency (RF) communication protocol, and/or other proprietary and non-proprietary communication protocols.

In one or more embodiments, the communication component 402 is configured to establish a secure, trusted telemetry connection with an external device (e.g., external device 116) prior to facilitating the exchange of sensitive data between the implantable device 104 and the external device using a non-proprietary telemetry communication protocol (e.g., BLUETOOTH®, BLE, and the like). In some embodiments, in order to establish such a secure, trusted connection, the implantable device 104 must first be paired with the external device (or otherwise have established a trusted relationship with the external device). According to these embodiments, the security component 404 can include pairing component 406 to facilitate trusted pairing the implantable device 104 with an external device to ensure the implantable device 104 performs secure telemetry communications with only authorized devices.

In the embodiment shown, the pairing component 406 can include negotiation component 408, validation component 410, regulation component 412 and removal component 414. The pairing component 406 can be configured to perform one or more standard pairing procedures defined by a non-proprietary telemetry communication protocol employed by the implantable device. For example, in embodiments in which the non-proprietary telemetry communication protocol is BLUETOOTH® or BLE, the pairing component 406 can be configured to perform a standard pairing procedure defined in the BLUETOOTH® or BLE specification (e.g., BLUETOOTH® SPECIFICATION Version 4.2 [Vol 1, Part A] 5.4.2 Key Generation, and BLUETOOTH® SPECIFICATION Version 4.2 [Vol 3, Part H] 3.6.1 Key Distribution and Generation). According to this example, based on reception of a pairing request or a connection request from an unpaired external device using BLUETOOTH® or BLE protocol, the pairing component 406 can be configured to initiate and/or perform the standard BLUETOOTH® or BLE associated with the request. In one or more embodiments, based on reception of a pairing request or a connection request from an unpaired external device, the negotiation component 408 can be configured to negotiate the encryption information to be used by the implantable device 104 and the external device 116 to establish a secure telemetry connection after the devices are paired. For example, the encryption information can include one or more encryption keys to be used by the implantable device 104 and the external device 116 for link layer encryption and/or application layer encryption in association with a secure telemetry session between the respective devices after the respective device are paired.

The validation component 410 can be configured to facilitate trusted pairing by executing an auxiliary validation procedure in association with performance of the standard (and commercially available) pairing procedure associated with a non-proprietary telemetry protocol (e.g., BLUETOOTH®, BLE, and the like). As described with reference to FIGS. 1, 2 and 3, this auxiliary validation procedure can employ the external device 116 and/or an associated verification device 302 providing extra validation information to the implantable device 104 in order to pair with the implantable device 104. The validation information can include for example, a specific code, password, or signal provided by the external device 116 or a verification device 302 to the implantable device 104. In some implementations, the validation information can indicate a remote server (e.g., remote server device 120) verified the external device or an entity operating the external device (e.g., as represented by a user account associated with the entity) as being authorized to establish the telemetry connection with the implantable device 104. In another implementation, the validation information can indicate an implantable device application of the external device determined the external device and/or an entity operating the external device is authorized to employ the external device to establish the telemetry connection with the implantable medical device. According to this implementation, the implantable device application can be configured to determine the entity is authorized based on reception of input, via the external device, that uniquely identifies the entity as an authorized entity (e.g., a username or password, biometric information, information input to the external device via another device such as an RFID tag, and the like).

Regardless of the form or origin of the validation information, the validation component 410 can be configured to interpret the validation information to determine if the correct validation information is received. For example, the validation component 410 can access information stored in memory that identifies one or more types of validation information as the providing authority for the validation component 410 to authorize pairing between the implantable device and the device that provides the validation information. Based on reception of the correct validation information in association with a pairing request, the validation component 410 can authorize pairing between the implantable device 104 and the external device and pairing component 406 can complete the pairing procedure.

Figure 5:
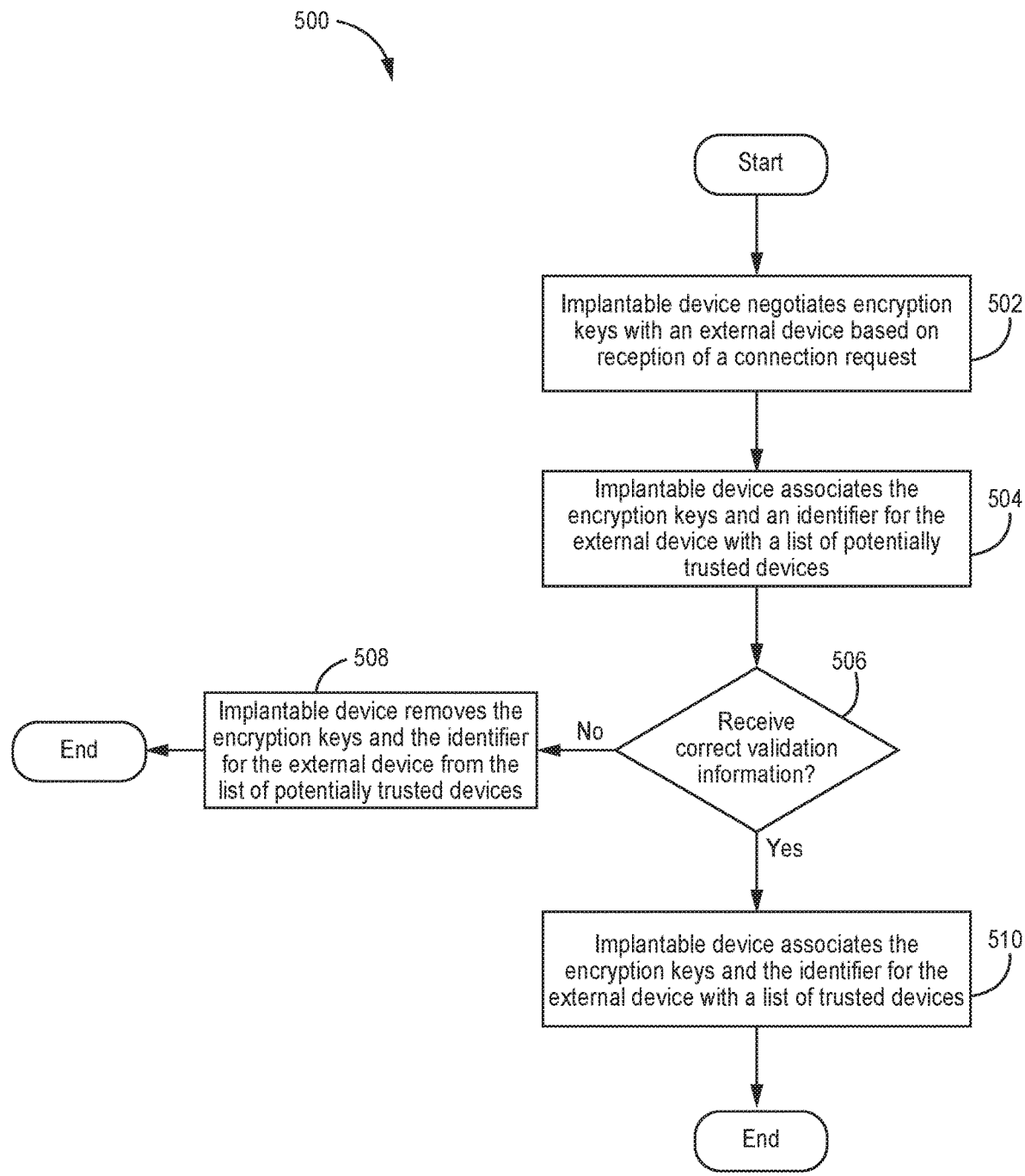
FIGS. 5 and 6 illustrate flow diagrams of additional example non-limiting methods that facilitate trusted pairing between an implantable device and an external device in accordance with one or more embodiments described herein.

FIG. 5 illustrates a flow diagram of an example non-limiting method 500 that facilitates trusted pairing between an implantable device and an external device in accordance with one or more embodiments described herein. While, for purposes of simplicity of explanation, the methodologies are shown and described as a series of acts, the disclosed subject matter is not limited by the order of acts, as some acts can occur in different orders and/or concurrently with other acts from that shown and described herein. For example, those skilled in the art will understand and appreciate that a methodology can alternatively be represented as a series of interrelated statuses or events, such as in a state diagram. Moreover, not all illustrated acts may be required to implement a methodology in accordance with the disclosed subject matter. Additionally, it is to be appreciated that the methodologies disclosed in this disclosure are capable of being stored on an article of manufacture to facilitate transporting and transferring such methodologies to computers or other computing devices.

In one or more embodiments, method 500 can be performed by implantable device 104 using communication component 402 and security component 404. With reference to FIGS. 4 and 5, method 500 exemplifies some of the features and functionalities of the pairing component 406, particularly with respect to the negotiation component 408 and the validation component 410. At 502, the implantable device (e.g., implantable device 104) negotiates encryption keys (e.g., via negotiation component 408) with an external device (e.g., external device 116) based on reception of a connection request from the external device. For example, the connection request can be a pairing request, or interpreted as a pairing request, depending on the specific telemetry protocol employed. It should be appreciated that the implantable device would respond with a different procedure if the implantable device has previously been paired with the external device that provided the connection request. Accordingly, method 500 is described with the assumption that the implantable device receives a pairing request or connection request from an external device that has not been previously paired with the implantable device. In various embodiments, the connection and/or pairing request is communicated to the implantable device 104 using a non-proprietary telemetry communication protocol (e.g., BLUETOOTH®, BLE, and the like), and includes a request to perform telemetry with the implantable device 104 using the non-proprietary telemetry communication protocol.

At 504, the implantable device associates the encryption keys and an identifier for the external device with a list of potentially trusted devices (e.g., via negotiation component 408). In particular, in accordance with the embodiment shown, the negotiation component 408 can be configured to initiate a standard pairing procedure (e.g., according to the non-proprietary telemetry protocol employed by the implantable device) based on reception of a pairing request. This standard pairing procedure can involve negotiating the security information that will be used by the respective device to perform a secure telemetry session if the devices are paired. For example, the implantable device 104 (e.g., via the negotiation component 408) can generate one or more encryption keys that will be used for link layer and/or application layer encryption between the respective devices. The implantable device 104 can further provide the one or more encryption keys to the external device (e.g., via communication component 402). Alternatively, the external device can generate the keys and provide the keys to the implantable device 104. The negotiation component 408 can further be configured to store information identifying the external device (e.g., a unique identifier for the external device) and the security information (e.g., the encryption keys) as first data in the memory 426 (e.g., in a defined file in the memory 426, in a defined data structure in the memory 426, in a defined portion of the memory 426, etc.) that indicates the external device is potentially a trusted device with which the implantable device 104 can pair. For example, this first data is identified in FIG. 5 as potentially trusted devices 428 data. In various implementations, the information identifying the external device (e.g., a unique identifier for the external device) is provided to the implantable device 104 in association with the connection and/or pairing request. In some embodiments, the communication component 402 can be configured to restrict the type of communication authorized between the implantable device 104 and the external device 116 based on association of the external device 116 with the potentially trusted devices 428 data. For example, in one embodiment, the communication component 402 can reject all transmissions from the external device 116 except transmissions that include validation information.

At 506, the implantable device determines whether it has received the correct validation information required for pairing with the external device (e.g., via validation component 410). For example, in one embodiment, the validation component 410 can direct the communication component 402 to send a request to the external device 116 for the validation information. The external device 116 can then respond by providing the validation information as requested if the external device is in fact configured to provide the validation information and can generate the correct validation information. According to this embodiment, the validation component 410 can be configured to send the request for the validation information at a defined point during the pairing procedure (e.g., after generation and exchange of the keys). In another embodiment, the external device 116 can be configured to provide the validation information in association with the pairing procedure. For example, an implantable device application of the external device 116 that is used to initiate the pairing request with the implantable device 104 can be configured to send the implantable device 104 the required validation information in association with the pairing procedure. The implantable device application would thus know when to provide the validation information and what validation information to provide. According to this implementation, the validation component 410 would not request the validation information from the external device 116 but simply wait for the external device (or verification device 302) to provide the validation information per procedure. In either of these embodiments, in some implementations, the validation component 410 can further require the external device 116 provide the validation information within a defined window of time (e.g., following reception of the connection request, following transmission of a request for the validation information, or following another defined event). With these implementations, at 506, the validation component 410 would determine whether the implantable device had received the correct validation information within the defined window of time.

In accordance with the embodiment described by method 500, if at 506, the implantable device 104 has not received the correct validation information (or has not received the correct validation information within the defined window of time in some implementations), method 500 proceeds to 508 wherein the implantable device 104 removes the encryption keys and the identifier for the external device 116 from the potentially trusted devices list. At this time, the communication component 402 can be configured to disable any connection between the implantable device 104 and the external device 116 and returns to operating as usual.

However, if at 506, the implantable device 104 receives the correct validation information (or receives the correct validation information within the defined window of time in some implementations), method 500 proceeds to 510 wherein the implantable device 104 associates the encryption keys and the identifier for the external device with a list of trusted devices. For example, if the validation component 410 receives the correct validation information, the validation component 410 can further be configured to store information identifying the external device (e.g., a unique identifier for the external device) and the security information (e.g., the encryption keys) as second data in the memory 426 (e.g., in a defined file in the memory 426, in a defined data structure in the memory 426, in a defined portion of the memory 426, etc.) that indicates the external device is a trusted device. This second data is identified in FIG. 5 as trusted devices 430 data. Based on association of the external device 116 with the trusted devices list, the external device 116 becomes officially paired with the implantable device 104. For example, based on association of the encryption keys and the identifier for the external device 116 with the trusted devices list, the communication component 402 can be configured to accept future requests from the external device 116 to establish telemetry connections with the implantable device 104 using the non-proprietary telemetry protocol (e.g., BLE) and without negotiating new encryption keys or requiring the external device 116 to provide the validation information or new validation information. In a telemetry session established between the implantable device 104 and a paired external device, the communication component 402 can be configured to allow communication of various type of information between the implantable device 104 and the paired external device, such a control data packets and application data packets. In one or more embodiments, after an external device is associated with the trusted devices list, it will remain paired with the implantable device 104 for an indefinite period of time unless the implantable device 104 receives an authorized request to remove the external device from the trusted devices list or the implantable device 104 is otherwise reprogrammed or reset.

In some implementations, the communication component 402 can be configured to send the external device an acknowledgment message indicating the external device is officially paired. In one embodiment, the communication component 402 can also be configured to maintain the connection between the implantable device 104 and the external device 116 for a defined period of time following successful pairing to receive potential downlink communications from the external device 116. Such downlink communications would be encrypted using the encryption keys negotiated in the pairing procedure. Similarly, the communication component 402 would encrypt uplink communication sent to the external device 116 using the encryption keys. In another embodiment, the communication component 402 can be configured to disable the connection following successful pairing. With this embodiment, the external device 116 can send the implantable device 104 a new connection request when it desires to communicate with the implantable device 104. However, because the external device 116 is now paired with the implantable device 104, the pairing procedure is skipped and the implantable device 104 and the external device 116 can establish a secure telemetry session using the encryption keys previously negotiated in the pairing procedure.

With reference again to FIG. 4, the regulation component 412 can be configured to police pairing requests received by the implantable device 104 over time to limit vulnerabilities to unauthorized third party devices. In particular, in some scenarios, unauthorized external devices that are configured to operate using the non-proprietary telemetry protocol employed by the implantable device 104 (e.g., BLUETOOTH®, BLE, and the like) may repeatedly send the implantable device pairing requests, either intentionally or inadvertently. This causes the implantable device 104 to initiate the pairing procedure and waste unnecessary battery power as well as tie up the ability for the communication component 402 to perform telemetry with authorized external devices. In order to limit minimize this risk, the regulation component 412 can be configured to identify an unauthorized external device that repeatedly sends the implantable device 104 pairing requests and block that unauthorized external device from sending the implantable device 104 any additional pairing or connection requests. For example, in one or more embodiments, the regulation component 412 can monitor or track pairing requests received by the implantable device 104 from external devices that fail to provide or timely provide the correct validation information. A pairing request that does not result in a successful pairing is referred to herein as a failed pairing attempt. The regulation component 412 can apply a predefined threshold allotment the maximum allowed failed pairing attempts. If an external device has reached the maximum amount of failed pairing attempts, the regulation component 412 can associate the unauthorized external device as third data in the memory 426 (e.g., in a defined file in the memory 426, in a defined data structure in the memory 426, in a defined portion of the memory 426, etc.) that identifies devices with which the implantable device 104 is not authorized to pair or otherwise communicate. This third data is identified in FIG. 5 as untrusted devices 432 data. With this embodiment, after an unauthorized external device is associated with the untrusted devices list, the communication component 402 can be configured ignore future pairing or connection requests received from the unauthorized external device.

Figure 6:
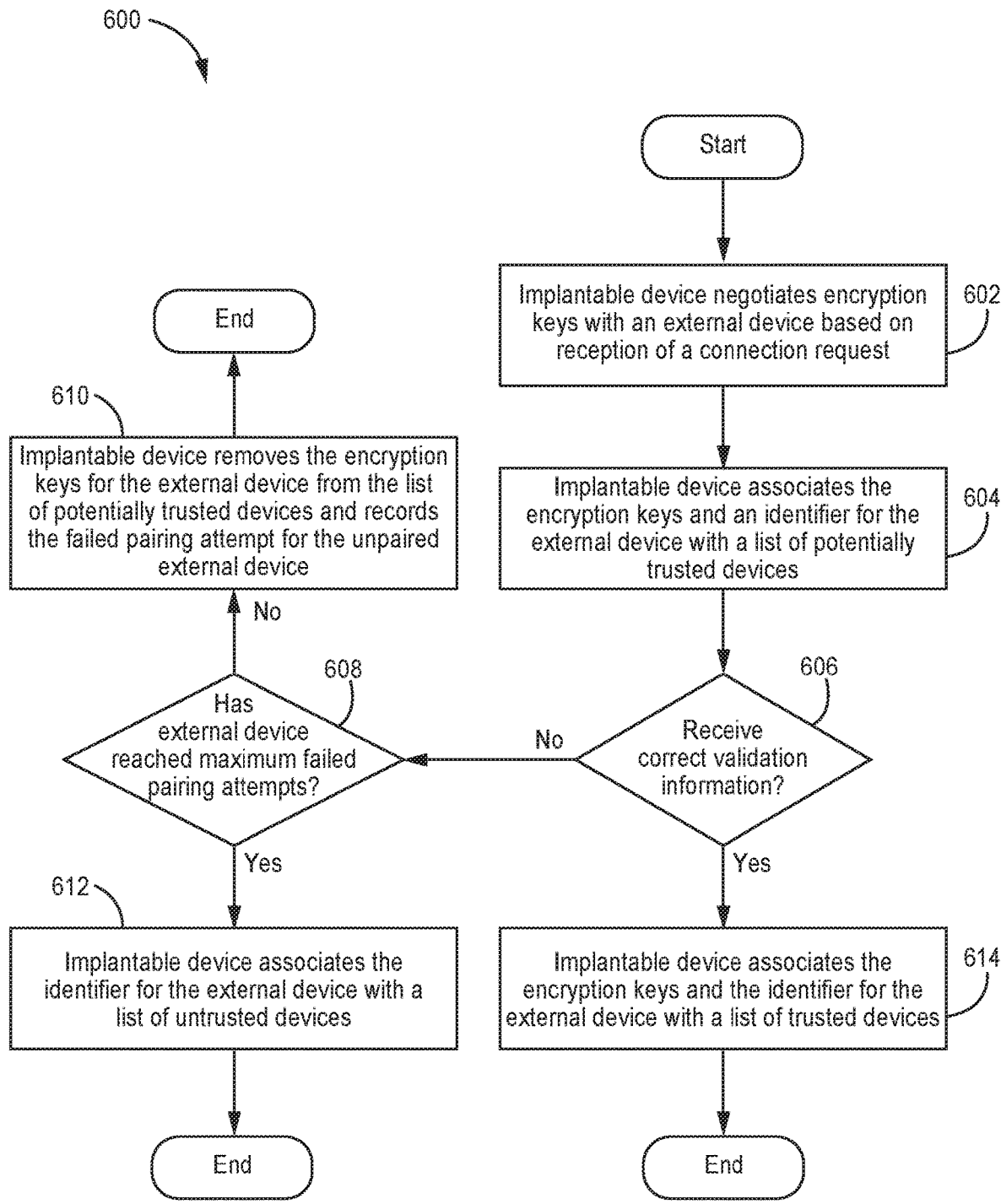

For example, FIG. 6 illustrates a flow diagram of another example non-limiting method 600 that facilitates trusted pairing between an implantable device and an external device in accordance with one or more embodiments described herein. In one or more embodiments, method 500 can be performed by implantable device 104 using communication component 402 and security component 404. With reference to FIGS. 4 and 6, method 600 exemplifies some of the features and functionalities of the pairing component 406, particularly with respect to the negotiation component 408, the validation component 410 and the regulation component 412. Method 600 includes same or similar steps as method 500. Similar to method 500, method 600 is described with the assumption that the implantable device 104 receives a pairing request or connection request from an external device that has not been previously paired with the implantable device 104. Repetitive description of like elements employed in respective embodiments is omitted for sake of brevity.

At 602, the implantable device (e.g., implantable device 104) negotiates encryption keys (e.g., via negotiation component 408) with an external device (e.g., external device 116) based on reception of a connection or pairing request from the external device. In various embodiments, the connection or pairing request is communicated to the implantable device 104 using a non-proprietary telemetry communication protocol (e.g., BLUETOOTH®, BLE, and the like), and includes a request to perform telemetry with the implantable device 104 using the non-proprietary telemetry communication protocol. At 604, the implantable device associates the encryption keys and an identifier for the external device with a list of potentially trusted devices (e.g., via negotiation component 408). For example, the negotiation component 408 can be configured to store information identifying the external device (e.g., a unique identifier for the external device) and the encryption keys as first data in the memory 426 (e.g., potentially trusted devices 428 data), that indicates the external device is potentially a trusted device with which the implantable device 104 can pair. In one embodiment, based on association of the external device 116 with the potentially trusted devices list, the communication component 402 can be configured to ignore information communicated to the implantable device by the external device other than the validation information.

At 606, the implantable device determines whether it has received the correct validation information required for pairing with the external device (e.g., via validation component 410). In some implementations, the validation component 410 can further require the external device 116 provide the validation information within a defined window of time (e.g., following reception of the connection request, following transmission of a request for the validation information, or following another defined event). With these implementations, at 606, the validation component 410 would determine whether the implantable device had received the correct validation information within the defined window of time.

In accordance with the embodiment described by method 600, similar to method 500, if at 606, the implantable device 104 receives the correct validation information (or receives the correct validation information within the defined window of time in some implementations), method 600 proceeds to 614 wherein the implantable device 104 removes the encryption keys and the identifier for the external device 116 from the potentially trusted devices list and associates the encryption keys and the identifier for the external device with a list of trusted devices. For example, if the validation component 410 receives the correct validation information, the validation component 410 can further be configured to store information identifying the external device (e.g., a unique identifier for the external device) and the security information (e.g., the encryption keys) as second data in the memory 426 that indicates the external device is a trusted device (e.g., the trusted devices 430 data). Based on association of the external device 116 with the trusted devices list, the external device 116 becomes officially paired with the implantable device 104 and the communication component 402 can be configured to accept future requests from the external device 116 to establish telemetry connections with the implantable device 104 using the non-proprietary telemetry protocol (e.g., BLE) and without negotiating new encryption keys or requiring the external device 116 to provide the validation information or new validation information.

However, unlike method 500, if at 606 the implantable device 104 has not received the correct validation information (or has not received the correct validation information within the defined window of time in some implementations), method 600 proceeds to decision block 608 wherein the implantable device 104 then determines whether the external device has reached the maximum amount of failed pairing attempts (e.g., via regulation component 412). For example, the regulation component 412 can access information stored in memory 426 of the implantable device that identifies one or more external devices and indicates the number of failed pairing attempts performed by the external device. The regulation component 412 can examine this failed pairing attempt information to determine whether the external device has had any previous failed pairing attempts and whether the number of failed pairing attempts is one less than the maximum allowed pairing attempts, making this current failed pairing attempt the last allowed failed pairing attempt (i.e., whether this failed pairing attempt was the third strike). If at 608 the regulation component 412 determines that the external device has not reached the maximum number of failed pairing attempts, method 600 proceeds to 610 and the implantable device removes the encryption keys and the identifier for the external device 116 from the potentially trusted devices list. In addition, the implantable device also records the failed pairing attempt for the external device in memory 426 of the implantable device 104 (e.g., in the failed pairing attempt information). However, if at 608 the implantable device determines that the external device has reached the maximum amount of failed pairing attempts (i.e., the current failed pairing attempt is the third strike), method 600 proceeds to 612. At 612, the implantable device associates the identifier for the external device with a list of untrusted devices (e.g., the untrusted devices 432 data in memory 426). The implantable device also removes the external device and the encryption keys from the list of potentially trusted devices. The list of untrusted devices characterizes the external device as unauthorized to establish future telemetry connections with the implantable medical device using the non-proprietary telemetry protocol. In accordance with one or more embodiments, the communication component 402 can be configured to ignore future requests from the external device to establish telemetry connections with the implantable medical device using the non-proprietary telemetry protocol based on association of the external device with the list of untrusted devices.

With reference back to FIG. 4, as previously described, after an external device is paired with the implantable device, the implantable device 104 can receive connection requests from the external device using the non-proprietary telemetry protocol (e.g., BLUETOOTH®, BLE, and the like), and skip the pairing procedure and the associated validation procedure. The respective devices can simply establish a secure telemetry connection using the non-proprietary telemetry protocol based on determination, by the implantable device, that the respective devices are paired. The respective devices can be configured to communicate in a secure manner by encrypting and decrypting uplink and downlink communications, respectively, using the one or more encryption keys established during the pairing procedure. In one or more embodiments, the authorization component 416 can be configured to determine whether the implantable device 104 has received a connection request from a paired external device. For example, the authorization component 416 can be configured to analyze connection requests received by the external device to determine whether the external device is associated with the trusted devices list (e.g., trusted devices 430 data). Based on a determination that the external device is associated with the trusted devices list, the authorization component 416 can authorize the communication component 402 to accept the connection request and the communication component 402 can then establish and conduct a secure telemetry session with the external device according to the non-proprietary telemetry communication protocol. If the authorization component 416 determines the connection request is received from an unpaired external device, the authorization component 416 can be configured to instruct the pairing component 406 to act upon the connection request as a pairing request. Depending on the particular implementation, the pairing component 406 would then perform operations according to methods 400 and 500.

Figure 7:
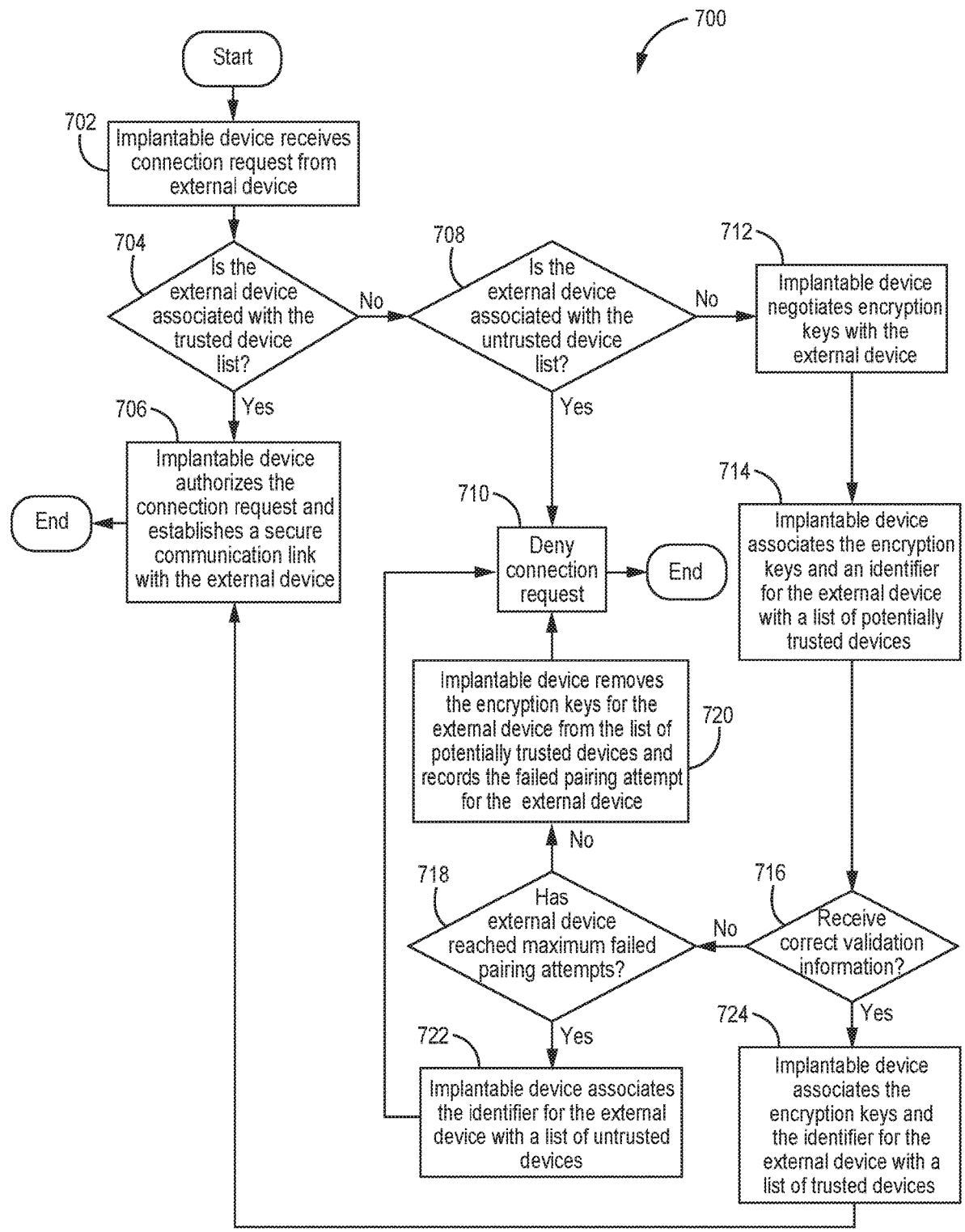
FIG. 7 illustrates a flow diagram of an example non-limiting method that facilitates establishing secure telemetry connections between an implantable device and an external device in accordance with one or more embodiments described herein.

FIG. 7 illustrates a flow diagram of an example non-limiting method 700 that facilitates establishing secure telemetry connections between an implantable device and an external device in accordance with one or more embodiments described herein. In one or more embodiments, method 700 can be performed by implantable device 104 using communication component 402 and security component 404. With reference to FIGS. 4 and 7, method 700 exemplifies some of the features and functionalities of the pairing component 406 and the authorization component 416. Unlike methods 500 and 600, method 700 is described in association with reception of a connection request that may be from a paired external device or an unpaired external device. Repetitive description of like elements employed in respective embodiments is omitted for sake of brevity.

At 702, the implantable device (e.g., implantable device 104) receives (e.g., via communication component 402) a connection request from an external device (e.g., external device 116). In various embodiments, the connection request is communicated to the implantable device 104 using a non-proprietary telemetry communication protocol (e.g., BLUETOOTH®, BLE, and the like), and includes a request to perform telemetry with the implantable device 104 using the non-proprietary telemetry communication protocol. At 704, the implantable device determines (e.g., via authorization component 416), whether the external device is associated with the trusted devices list (e.g., trusted devices 430 data) and thus has previously paired with the implantable device or otherwise established a trusted telemetry relationship with the implantable device. If at 704 the implantable device determines that the external device is associated with the trusted devices list, method 700 proceeds to 706 and the implantable device can be configured to authorize (e.g., via authorization component 416) the connection request and establishes a secure communication link with the external device. For example, the authorization component 416 can check to see whether an identifier for the external device is associated with the trusted devices 430 data. The identifier for the external device can be provided to the implantable device with the connection request. If the identifier for the external device is associated with the trusted devices 430 data, authorization component 416 can be configured to direct the communication component 402 to establish a secure telemetry connection with the implantable device using the non-proprietary telemetry protocol. The communication component 402 can perform the secure telemetry session by encrypting and decrypting uplink and downlink communications, respectively, communicated between the implantable device and the external device using the encryption keys previously determined during the pairing process and associated with the implantable device identifier in the trusted devices 430 data.

If at 704 the implantable device determines the external device is not associated with the trusted devices list, method 700 proceeds to decision block 708. At decision block 708, the implantable device determines whether the external device is associated with the untrusted devices list (e.g., untrusted devices 432 data). For example, the authorization component 416 can determine whether the identifier for the external device is associated with the untrusted devices 432 data. If the implantable device determines that the external device is associated with the untrusted devices list, then method 700 proceeds to 710 and the implantable device denies the connection request.

If at 708 the implantable device 104 determines that the external device is not associated with the untrusted devices list, method 700 can proceeds according to the pairing process described by method 600. For example, if at 708 the implantable device 104 determines that the external device is not associated with the untrusted devices list, at 712 the implantable device negotiates encryption keys (e.g., via negotiation component 408) with the external device (e.g., external device 116). At 714, the implantable device associates the encryption keys and an identifier for the external device with the list of potentially trusted devices (e.g., via negotiation component 408). At 716, the implantable device determines whether it has received or timely received the correct validation information required for pairing with the external device (e.g., via validation component 410). If at 716 the implantable device 104 receives or timely receives the correct validation information, method 700 proceeds to 724 wherein the implantable device 104 removes the encryption keys and the identifier for the external device 116 from the potentially trusted devices list and associates the encryption keys and the identifier for the external device with a list of trusted devices. Based on association of the external device 116 with the trusted devices list, the external device 116 becomes officially paired with the implantable device 104 and the communication component 402 can be configured to accept future requests from the external device 116 to establish telemetry connections with the implantable device 104 using the non-proprietary telemetry protocol (e.g., BLE) and without negotiating new encryption keys or requiring the external device 116 to provide the validation information or new validation information. According to method 700, based on association of the external device with the trusted devices list, the implantable device can further proceed to authorize the connection request and establish a secure communication link with the external device at 706.

If at 716 the implantable device 104 has not received or timely received the correct validation information, method 700 proceeds to decision block 718 wherein the implantable device 104 then determines whether the external device has reached the maximum amount of failed pairing attempts (e.g., via regulation component 412). If at 718 the regulation component 412 determines that the external device has not reached the maximum number of failed pairing attempts, method 700 proceeds to 720 and the implantable device removes the encryption keys and the identifier for the external device 116 from the potentially trusted devices list. In addition, the implantable device also records the failed pairing attempt for the external device in memory 426 of the implantable device 104 (e.g., in the failed pairing attempt information). The implantable device further proceeds to deny the connection request at 710. However, because the external device is not associated with the untrusted devices list, the external device can send a new pairing or connection request to the implantable device to attempt. However, if at 718 the implantable device determines that the external device has reached the maximum amount of failed pairing attempts (i.e., the current failed pairing attempt is the third strike), method 700 proceeds to 722. At 722, the implantable device associates the identifier for the external device with a list of untrusted devices (e.g., the untrusted devices 432 data in memory 426). The implantable device also removes the external device identifier and the encryption keys from the list of potentially trusted devices and denies the connection request at 710. In accordance with the embodiment shown, the communication component 402 can be configured to immediately deny future requests from the external device based on association of the external device with the list of untrusted devices.

Referring again to FIG. 4, in some scenarios, it may be necessary to "unpair" or otherwise remove an external device and/or user account that has been paired with the implantable device 104. For example, an external device (e.g., external device 116) that is paired with the implantable device may become lost, stolen, sold, or otherwise susceptible to operation by an entity that is not authorized to use the external device to communicate with the implantable device 104. In other scenarios, an external device or user account that is actually authorized to pair with the implantable device 104 may become associated with the untrusted devices list do to a variety of technical, user entry or administrative errors. In view of these scenarios, the pairing component 406 can include removal component 414 to facilitate removing an external device from the trusted devices or untrusted devices list. In various embodiments, the removal component 414 can be configured to remove a device from the trusted or untrusted devices list using a same or similar mechanism used to add an external device to the trusted devices or untrusted devices list.

For example, in one or more embodiments, in order to remove an external device from the trusted devices or untrusted devices list, the removal component 414 can receive a removal request. In some embodiments, this removal request can be sent by any suitable external device employing the non-proprietary telemetry communication protocol (e.g., BLE). In other embodiments, only certain authoritative devices can be configured to provide the removal request. The removal request can include information identifying the external to be removed and the particular list (e.g., either untrusted or trusted), that the external device is to be removed from. In one embodiment, the removal request can identify two or more devices to be removed from the trusted devices list or the untrusted devices list. In some implementations, the device/entity providing the removal request can request that it (i.e., the device itself), be removed from the untrusted or trusted devices list. In other embodiments, the device/entity providing the removal request can request that a different device be removed from the untrusted or trusted devices list. For example, if an external device that was previously paired with the implantable device is lost, a user may be provided a new external device. Using the new external device, the user can send a removal request that requests the old implantable device be removed from the trusted devices list.

Similar to the mechanism for pairing with the implantable device 104, in order to remove an external device from the trusted devices or untrusted devices list, the removal component 414 can be configured to require the removal request be accompanied by validation information that indicates the entity (e.g., device and/or user account) providing the removal request is authorized to apply the removal request. The type of validation information can include same or similar types of validation information required for the pairing procedure (e.g., a unique password, a pass-code, secret key, a unique signal that represents a validation command, etc.). The mechanisms for generating this validation information can be the same or similar to those described for generating the validation information required for pairing. For example, in some implementations, the validation information needed for removal can be provided to the external device from the remote server device 120 in response to performance of authorization procedure by the remote server device. In another example, the validation information needed for removal can be generated by the external device in association with an authorization procedure performed by the external device (e.g., via an implantable device application) in response to user input at the external device. In another example, the validation information needed for removal can be provided by an auxiliary verification device (e.g., verification device 302). In some embodiments, the specific validation information (e.g., the password, the key, the unique signal, etc.) can be the same as that required for pairing. In other embodiments, the removal component 414 can require different validation information (e.g., a different password, a different key, a different signal), for removal. The implantable device 104 can further store predefined removal information that associates certain validation information with authority to remove a device from the trusted devices and/or untrusted devices list. Accordingly, based on reception of a removal request that is accompanied by the correct validation information, the removal component 414 can be configured to remove the requested device from the requested list.

Figure 8:
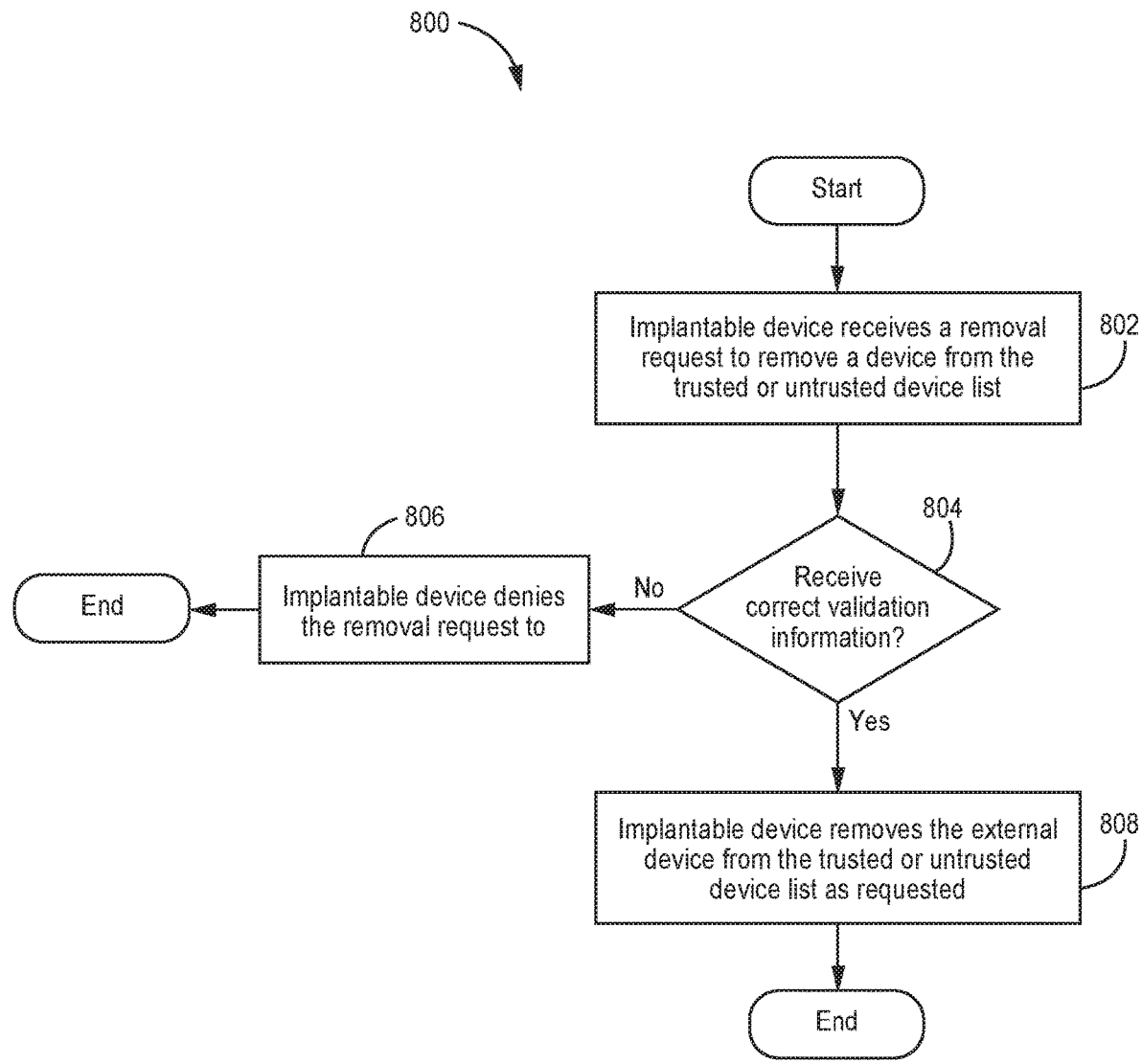
FIG. 8 illustrates a flow diagram of an example non-limiting method that facilitates removing an external device from a trusted devices list or an untrusted devices list in accordance with one or more embodiments described herein.

FIG. 8 illustrates flow diagram of an example non-limiting method 800 that facilitates removing an external device from a trusted devices list or an untrusted devices list in accordance with one or more embodiments described herein. In one or more embodiments, method 800 can be performed by implantable device 104 using communication component 402 and security component 404. With reference to FIGS. 4 and 8, method 800 particularly exemplifies some of the features and functionalities of removal component 414. Repetitive description of like elements employed in respective embodiments is omitted for sake of brevity.

At 802, the implantable device receives a removal request to remove a device from the trusted devices or untrusted devices list. In various implementations, this request can be sent from an external device (e.g., external device 116) using a non-proprietary telemetry communication protocol. In some embodiments, the removal request can only be received during a secure telemetry session from an external device that is paired with the implantable device 104. Based on reception of the removal request, in some embodiments, the implantable device 104 can be configured to send a response to the device requesting the validation information required for the removal. In other embodiments, the device can be configured to include the validation information in the removal request. At 804, the implantable device determines (e.g., via removal component 414) whether the correct validation information was received. In some embodiments, the removal component can also require the validation information to be received within a define time window. If at 804 the implantable device determines the correct validation information was received or was received within the defined window, then the implantable device can proceed to remove the device from the trusted or untrusted devices list as requested at 808. If however at 804 the implantable device determines the correct validation information was not received or was not received within the defined time window, then the implantable device can proceed to deny the removal request at 806.

With reference again to FIG. 4, in some embodiments, in order to facilitate regulating communication between the implantable device 104 and authorized or unauthorized external devices, the implantable device 104 can be configured to restrict the number of devices that can be associated with the trusted devices list and the untrusted devices list. According to these embodiments, the implantable device 104 can have a maximum number of devices that the implantable device 104 can be paired with at a time (i.e., associated with the trusted devices list). In one implementation, if the implantable device 104 has reached the maximum number of paired devices, the implantable device 104 can be configured to reject any new pairing requests. In another implementation, if the implantable device 104 has reached the maximum number of paired devices and the implantable device 104 receives a new pairing request from an authorized device that provides the correct validation information, the implantable device 104 can be configured to remove a previously paired external device from the trusted devices list and add the new external device to the trusted devices list. According to this implementation, the implantable device 104 can select the external device to remove based on duration of time the external device has been paired with the implantable device, frequency of communication with the implantable device, type of communication with the implantable device, or another suitable valuation metric. For example, the implantable device 104 can be configured to remove an external device that has been paired with the implantable device for the longest relative to the other external devices on the trusted devices list. In another example, the implantable device can be configured to remove the external device with which the implantable device 104 communicates with the least frequently. In another implementation, if the implantable device 104 has reached the maximum number of paired devices and the implantable device 104 receives a new pairing request from an authorized device that provides the correct validation information, the implantable device 104 can be configured to add the new external device to the trusted devices list and remove all previously paired external devices from the trusted devices list. As a result, any external device that was previously paired with the implantable device will have to perform the pairing procedure again in order to become re-paired with the implantable device 104. In this regard, the implantable device 104 naturally resets the trusted devices list as a safety mechanism to ensure that only trusted devices can communicate with the implantable device.

Similarly, the implantable device 104 can be configured to have maximum number of devices for association with the untrusted devices list. In one implementation, if the implantable device 104 has reached the maximum number of untrusted devices associate with the untrusted devices list, the implantable device 104 can go into a safe operation mode of some kind. For example, the implantable device 104 can restrict communication to only existing trusted devices and no longer accept new pairing request from any device for a defined period of time.

The implantable device 104 can further include a suitable power source 420 to drive the functionality of implantable device 104 and to provide power to the various electrical components of the implantable device 104. In one or more embodiments, the power source 420 includes but is not limited to, a battery, a capacitor, a charge pump, a mechanically derived power source (e.g., microelectromechanical systems (MEMs) device), or an induction component. The various embodiments described herein can provide improved management of power associated with the power source 420. For example, the mechanism of adding repeat offenders to the untrusted devices 432 data list prevents or minimizes unnecessary and excessive usage of the power source 420 of the implantable device 104, thereby increasing the lifespan of the implantable device 104.

The implantable device 104 can also include various other implantable device circuitry/hardware 422 to facilitate operation of the various components of the implantable device 104. For example, the other implantable device circuitry/hardware 518 can include, but is not limited to: a pulse generator, capacitors, leads (e.g., leads 110a,b), electrodes (e.g., tip electrodes 112a,b and ring electrodes 114a, b), sensors, accelerometers, pumping mechanisms, reservoirs, communication component 402 related hardware (e.g., antennas, transmitters, receivers, transceivers repeaters, etc.), a therapy output module, and the like. The other implantable device circuitry/hardware 422 can facilitate various operations of the implantable device, including, but not limited to, medical related operations (e.g., sensing electrical signals of the heart, dispensing a drug, etc.), and telemetry communication mode operations of the implantable device (e.g., RF telemetry and non-RF telemetry such as induction, optical based, audio based, vibration based, etc.).

Figure 9:
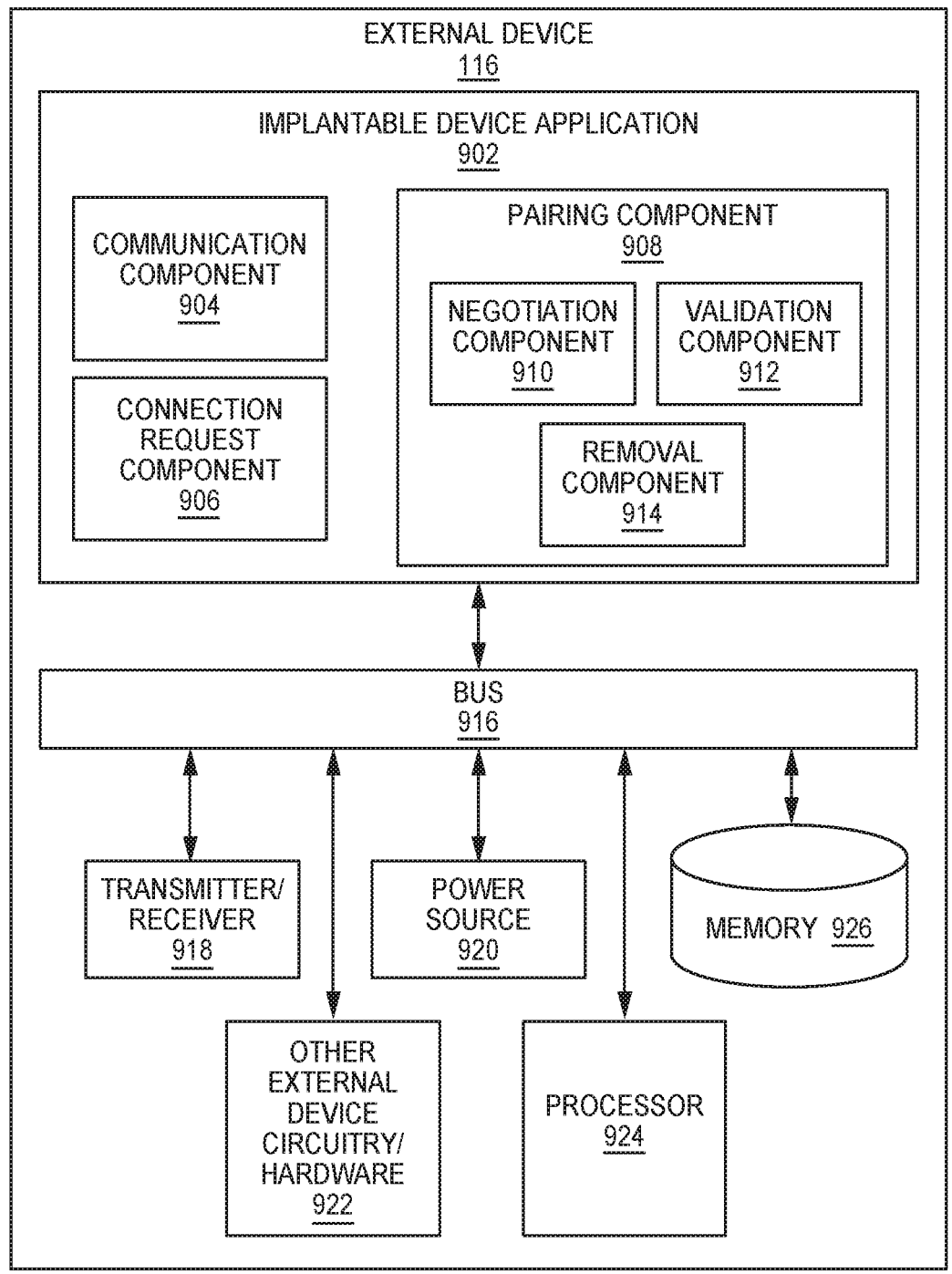
FIG. 9 illustrates a block diagram of an example, non-limiting external device in accordance with one or more embodiments described herein.

FIG. 9 illustrates a block diagram of an example, non-limiting external device (e.g., external device 116) in accordance with one or more embodiments described herein. The external device 116 can include an implantable device application 902 that is configured to provide various services associated with an implantable device (e.g., implantable device 104). In accordance with the subject disclosure, at least one of these services can include performing telemetry with an implantable device to obtain data from the implantable device (e.g., sensed physiological data, performance data, and the like). In another example, the implantable device application 902 can be configured to facilitate programming the implantable device using telemetry. In association with facilitating telemetry with an implantable device using a non-proprietary telemetry protocol, the implantable device application 902 can also be configured to facilitate pairing the external device 116 and/or a user account associated with the implantable device application 902, with the implantable device in accordance with the various trusted pairing techniques described herein. In some embodiments, the implantable device application 902 can also facilitate receiving one or more services and/or access to information provided by a remote server device (e.g., remote server device 120). According to these embodiments, the remote server device can provide one or more services and/or information related to an implantable device and/or a patient wearing an implantable device. For example, the remote server device can maintain information regarding patient identities, implantable device respectively worn by patients, and external devices and/or user accounts associated with the patients that are authorized to perform telemetry with the respective implantable devices. The remote server device can also control pairing between an implantable device and an external device by providing validation information to the external device 116 or providing the implantable device application 902 authorization to generate the validation information. In another example, the remote server device can receive collate and process information gathered by implantable devices.

The external device 116 can also includes a transmitter/receiver 918 (or transceiver), a power source 420, and other external device circuitry/hardware 922. The external device 116 can further include memory 926 configured to store computer executable components and instructions (e.g., the implantable device application 902) and a processor 924 to facilitate operation of the instructions (e.g., computer executable components and instructions) by the external device 116. The external device 116 can include a bus 916 that couples the various components of the implantable device 104, including, but not limited to, the implantable device application 902, the transmitter/receiver 918, the power source 920, the other external device circuitry/hardware 922, the processor 924 and the memory 926. Repetitive description of like elements employed in other embodiments described herein is omitted for sake of brevity.

In the embodiment shown, the implantable device application 902 includes communication component 904, connection request component 906 and pairing component 908. Similar to the communication component 402 of the implantable device 104, communication component 904 can be configured to facilitate telemetry communication between the external device 116 and one or more implantable devices (e.g., implantable device 104). The communication component 904 can also facilitate wired and/or wireless communication between the external device and one or more other external devices (e.g., remote server device 120 and various other types of devices). For example, the communication component 904 can be configured to control operation of the transmitter/receiver 918 (or transceiver) to facilitate establishing a telemetry connection with the implantable device 104 and controlling transmission and reception of data packets by the external device 116. The type of the transmitter/receiver 918 can vary depending on the type of telemetry protocol the implantable external device is configured to employ. In some embodiments, the transmitter/receiver 918 can be configured to perform different types of telemetry protocols (e.g., proprietary, non-proprietary, BLUETOOTH®, BLE, Wi-Fi, cellular, etc.). In other embodiments, the external device 116 can include a plurality of different transmitters/receivers that are respectively configured to perform different types of telemetry communication protocols. In some embodiments, rather than including a transmitter and a receiver that do not share common circuitry, the external device 116 can include a transceiver.

The communication component 904 can be configured to facilitate telemetry communication between the external device 116 and an implantable device 104 using a variety of telemetry communication protocols including proprietary and non-proprietary telemetry protocols. For example, in one or more embodiments, communication component 402 can communicate with external device 116 using NFC, or another type of communication protocol over a PAN or a LAN (e.g., a Wi-Fi network) that can provide for communication over greater distances than NFC protocol or that can provide various advantages (such as increased security).

In some embodiments, the communication component 904 can control transmission and reception of data packets via a communication channel associated with a communication protocol utilizing lower energy consumption than a conventional communication protocol for wirelessly transmitting data. For example, in a non-limiting example, communication component 904 controls transmission and reception of data packets using BLE protocol. Other communication protocols that can be employed by communication component 904 to communicate with an implantable device or another device can include, but are not limited to, other BLUETOOTH® communication protocols, a Session Initiation Protocol (SIP) based protocol, a Zigbee® protocol, a RF4CE protocol, a WirelessHART protocol, a 6LoWPAN (IPv6 over Low power Wireless Personal Area Networks) protocol, a Z-Wave protocol, an ANT protocol, an ultra-wideband (UWB) standard protocol, a radio frequency (RF) communication protocol, and/or other proprietary and non-proprietary communication protocols. In some embodiments, the communication component 904 can be configured to read RFID tags as input.

The implantable device application 902 can include connection request component 906 to facilitate sending connection request to an implantable device. For example, in one or more embodiments, in order to connect to or otherwise initiate a telemetry session with an implantable device using a non-proprietary telemetry communication protocol (e.g., BLE), a user of the external device 116 can open the implantable device application 902 and select a "connection request" function of the application. In some implementation, in order to employ the implantable device application 902 to initiate a connection request, the user of the implantable device application 902 must have a registered user account and be logged in to his or her user account (e.g., based on entry of username or password information or the like). Based on selection of the connection request function, in some implementations, the connection request component 906 can identify any implantable devices are within transmission range of the external device 116. The connection request component 906 can further present information identifying the one or more nearby implantable devices. Using the implantable device application 902, the user can the select a particular identified implantable device to connect to and select a "request connection" soft button or otherwise provide some form or input that is interpreted by the connection request component 906 as a request to establish a connection with the selected implantable device. Based on the input, the connection request component 906 can be configured to direct the communication component 904 to configure and send (e.g., using the transmitter/receiver 918) a connection request to the implantable device in accordance with the non-proprietary telemetry communication protocol (e.g., BLE).

In some embodiments, if the external device and/or the particular user account employed by the user was previously paired with the implantable device, the connection request component 906 can direct the communication component 904 to establish a secure telemetry connection with the implantable device using previously determined encryption keys for the external device and/or user account and the implantable device 104. These encryption keys can be stored in memory 926 of the external device for example, and accessed by the communication component 904. In implementations in which the external device 116 and/or the user account has not been paired with the implantable device, the connection request component 906 can direct the communication component 904 to send the selected implantable device a pairing request.

The pairing component 908 can be configured to facilitate the pairing process between the external device 116, and/or a user account associated with the implantable device application 902, and a selected implantable device in association with a pairing request. In particular, in accordance with various embodiments described herein, the communication component 904 can be configured to establish a secure, trusted telemetry connection with an implantable device (e.g., implantable device 104) prior to facilitating the exchange of sensitive data between the implantable device 104 and the external device 116 using a non-proprietary telemetry communication protocol (e.g., BLUETOOTH®, BLE, and the like). In some embodiments, in order to establish such a secure, trusted connection, the external device 116 and/or a user account associated with the external device 116 must first be paired with the implantable device 104 (or otherwise have established a trusted relationship with the implantable device). According to these embodiments, the pairing component 908 can be configured to facilitate trusted pairing between the external device and/or a user account associated with the implantable device application 902, and the implantable device 104.

Similar to the pairing component 406 of the implantable device 104, the pairing component 908 can include a negotiation component 910, a validation component 912, and a removal component 914. The pairing component 908 can be configured to perform one or more standard pairing procedures defined by a non-proprietary telemetry communication protocol employed by the implantable device. For example, in embodiments in which the non-proprietary telemetry communication protocol is BLUETOOTH® or BLE, the pairing component 908 can be configured to perform a standard pairing procedure defined in the BLUETOOTH® or BLE specification (e.g., BLUETOOTH® SPECIFICATION Version 4.2 [Vol 1, Part A] 5.4.2 Key Generation, and BLUETOOTH® SPECIFICATION Version 4.2 [Vol 3, Part H] 3.6.1 Key Distribution and Generation). According to this example, in association with sending a pairing request to an implantable device by the communication component 904, the pairing component 908 can be configured to initiate and/or perform the standard BLUETOOTH® or BLE associated with the pairing request. This can include negotiate of the encryption information to be used by the implantable device 104 and the external device 116 and/or a user account associated with the implantable device application 902 to establish a secure telemetry connection after the devices are paired. The negotiation component 910 can be particularly configured to negotiate the encryption information and store information in memory 926 associating the implantable device with the encryption information. For example, the encryption information can include one or more encryption keys to be used by the implantable device 104 and the external device 116 for link layer encryption and/or application layer encryption in association with a secure telemetry session between the respective devices after the respective device are paired.

Similar to the validation component 410, the validation component 912 can be configured to facilitate trusted pairing by executing an auxiliary validation procedure in association with performance of the standard (and commercially available) pairing procedure associated with a non-proprietary telemetry protocol (e.g., BLUETOOTH®, BLE, and the like). As described with reference to FIGS. 1-3, this auxiliary validation procedure can require the external device 116 and/or an associated verification device 302 to provide extra validation information to the implantable device 104 in order to pair with the implantable device 104. The validation information can include for example, a specific code, password, or signal provided by the external device 116 or a verification device 302 to the implantable device 104. In one or more embodiments, the validation component 912 can be configured to generate and/or obtain the validation information required for pairing the external device 116, and/or a user account associated with the implantable device application 902, with an implantable device. The validation component 912 can further be configured provide (e.g., using the communication component 904 and the transmitter/receiver 918) the validation information to the implantable device in association with a pairing procedure. In other embodiments, the validation component 912 can be configured to facilitate provision of validation information by an auxiliary verification device (e.g., verification device 302) to the implantable device in association with the pairing procedure.

For example, in some implementations, prior to sending of the pairing request or in association with sending the pairing request, the validation component 912 can be configured to initiate an authorization procedure with a remote server device (e.g., remote server device 120) to either receive the validation information from the remote server device or receive a command authorizing the validation component 912 to generate the validation information. According to these implementations, the validation component 912 can send (e.g., using communication component 904 and the transmitter/receiver 918) a request to the remote server device requesting the validation information and/or authorization to generate the validation information. The request can include information identifying the external device and/or the user account associated with the external device, and the implantable device. Based on reception of the request, the remote server device can perform an authorization procedure to determine whether the external device/user account is authorized to pair with the implantable device. Based on a determination that the external device and/or user account is authorized, the remote server device can provide the validation information to the validation component 912 and/or authorize the validation component 912 to generate the validation information.

In another implementation, prior to performing a pairing procedure and/or in association with performing a pairing procedure, the validation component 912 can be configured to generate and/or access previously defined validation information for the external device 116 and/or a user account associated with the implantable device application based on user input received at the external device 116. For example, prior to performing a pairing procedure and/or in association with performing a pairing procedure, the validation component 912 can generate a prompt requesting reception of user input that verifies the identity of the user operating the external device and/or otherwise indicates the user is authorized to pair with the implantable device. As previously discussed, this user input can be in the form of a username or password, biometric information, information input to the external device via another device such as an RFID tag, and the like. The validation component 912 can further have access to information stored in memory 926 that associates the user input with authorization to pair with the implantable device. According to this implementation, based on reception of the correct user input, the validation component 912 can be configured to generate and/or provide the correct validation information to the implantable device in association with a pairing procedure.

In another implementation, in association with a pairing procedure, the validation component 912 can generate a prompt that requests the validation information be provided to the implantable device via a dedicated auxiliary verification device (e.g., verification device 302). For example, in association with the pairing procedure, the implantable device 104 can be configured to send a request to the implantable device requesting the validation information. Based on reception of the request, the validation component 912 can generate a prompt requesting the user of the external device or another user provide the validation information using the auxiliary verification device at this time. The validation component 912 can also be configured to generate a notification when the validation information is received and accepted by the implantable device 104.

The removal component 914 can be configured to facilitate removing a device from the trusted or untrusted devices list using a same or similar mechanism used to pair an external device and/or user account with the implantable device. For example, in one or more embodiments, in order to remove an external device from the trusted devices or untrusted devices list, the removal component 494 can be configured to generate a removal request. In some embodiments, this removal request can be sent by the communication component 904 using the same non-proprietary telemetry communication protocol (e.g., BLE) associated with pairing. The removal request can include information identifying the external to be removed and the particular list (e.g., either untrusted or trusted), that the external device is to be removed from. In one embodiment, the removal request can identify two or more devices to be removed from the trusted devices list or the untrusted devices list. In some implementations, the device/entity providing the removal request can request that it (i.e., the device itself), be removed from the untrusted or trusted devices list. In other embodiments, the device/entity providing the removal request can request that a different device be removed from the untrusted or trusted devices list. For example, if an external device that was previously paired with the implantable device is lost, a user may be provided a new external device. Using the new external device, the user can send a removal request that requests the old implantable device be removed from the trusted devices list.

Similar to the mechanism for pairing with the implantable device 104, in order to remove an external device from the trusted devices or untrusted devices list, the removal component 914 can be configured to provide or facilitate providing (e.g., by a verification device 302) validation information with the removal request that indicates the entity (e.g., device and/or user account) providing the removal request is authorized to apply the removal request. The type of validation information can include same or similar types of validation information required for the pairing procedure (e.g., a unique password, a pass-code, secret key, a unique signal that represents a validation command, etc.). The mechanisms for generating and/or obtaining this validation information can be the same or similar to those described for generating the validation information required for pairing. For example, in some implementations, the validation information needed for removal can be provided to the external device from the remote server device 120 in response to performance of authorization procedure by the remote server device. In another example, the validation information needed for removal can be generated by the removal component 914 in association with an authorization procedure performed by the external device (e.g., via an implantable device application) in response to user input at the external device. In another example, the validation information needed for removal can be provided by an auxiliary verification device (e.g., verification device 302). In some embodiments, the specific validation information (e.g., the password, the key, the unique signal, etc.) can be the same as that required for pairing. In other embodiments, the removal component 914 can require different validation information (e.g., a different password, a different key, a different signal), for removal.

The external device 116 can further include a suitable power source 920 to drive the functionality of the external device 116 and to provide power to the various electrical components of the external device 116. In one or more embodiments, the power source 920 includes but is not limited to, a battery, a capacitor, a charge pump, a mechanically derived power source (e.g., microelectromechanical systems (MEMs) device), or an induction component. The external device 116 can also include various other external device circuitry/hardware 922 to facilitate operation of the various components of the implantable device 104. For example, the other external device circuitry/hardware 922 can include one or more suitable input devices (e.g., touchscreen, hard buttons, soft buttons, voice input), a display, an RFID reader, a biometric reader, a camera, and various other types of hardware elements found in conventional smart phones, tablets, laptop PCs, VR devices, wearable physiological monitoring devices, and the like, examples of which can be found with reference to FIG. 13.

Figure 10:
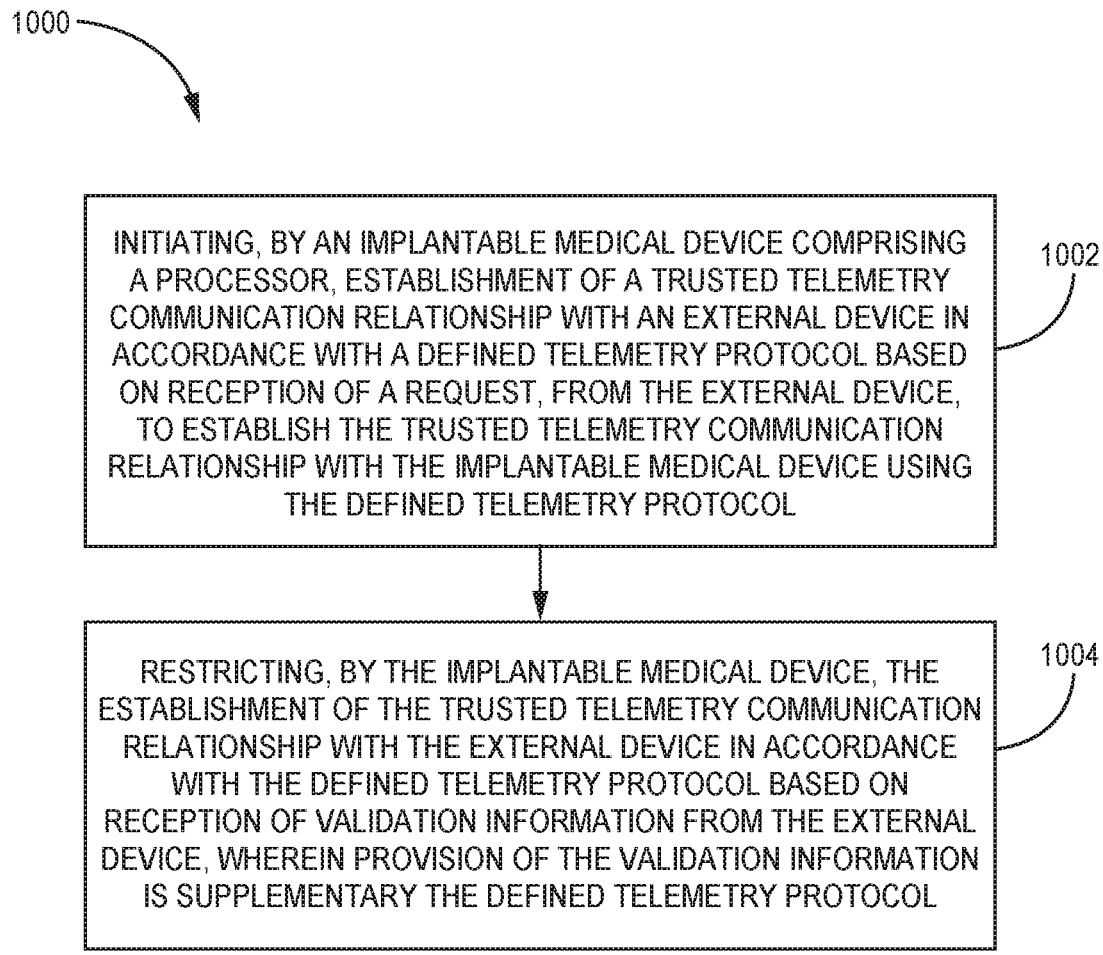
FIGS. 10, 11 and 12 illustrate additional flow diagrams of example, non-limiting methods that facilitate trusted pairing between an implantable device and an external device in accordance with one or more embodiments described herein.
Figure 11:
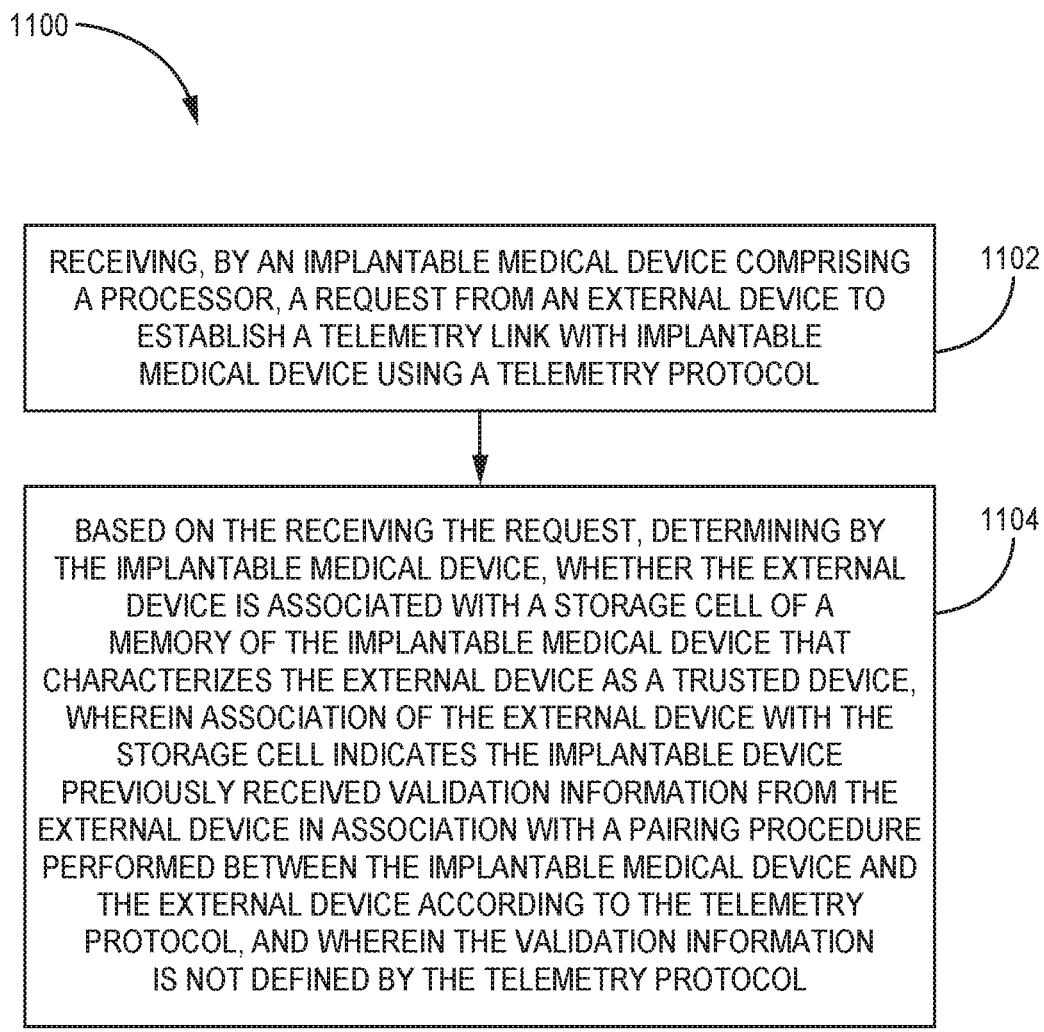
Figure 12:
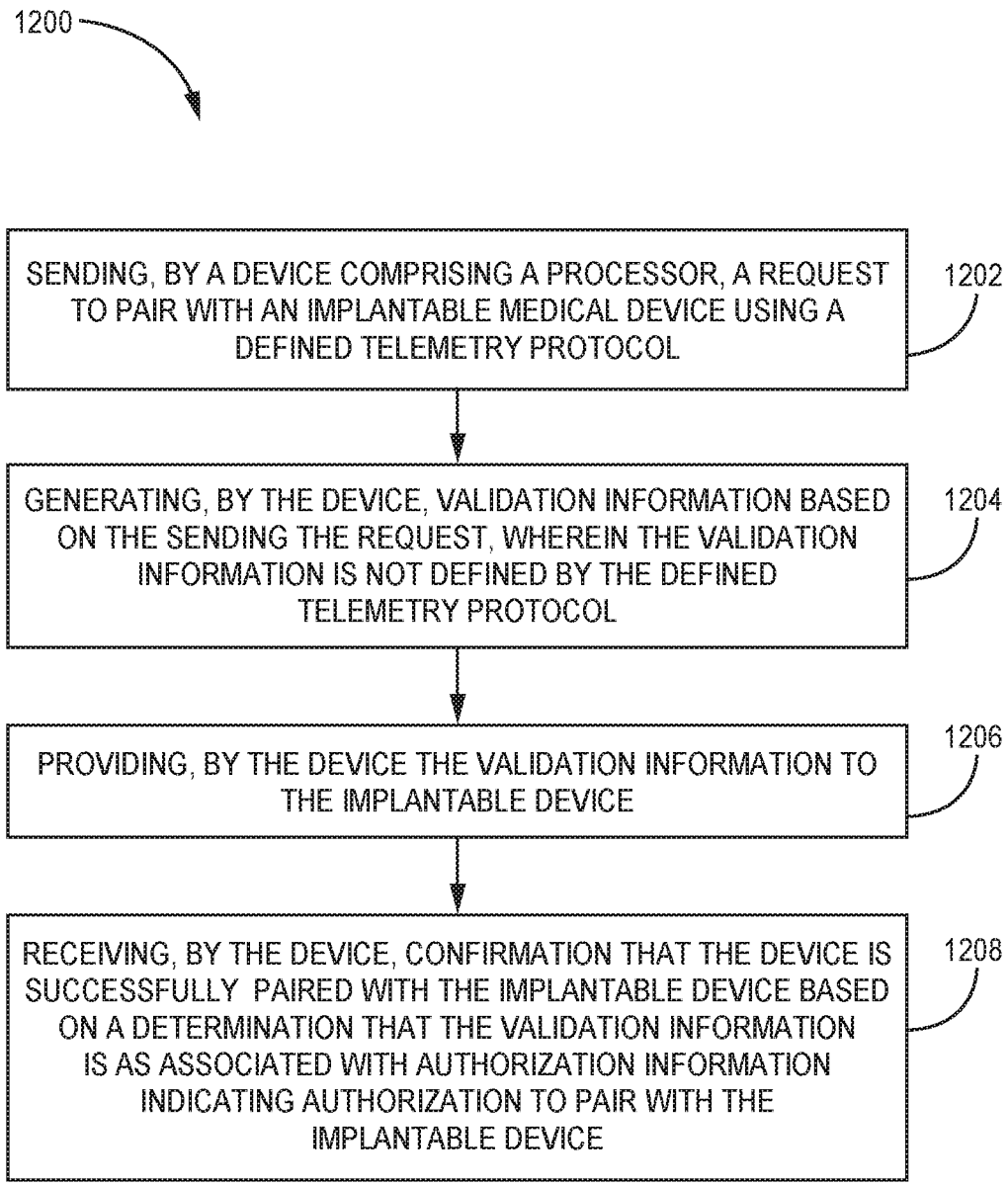

FIGS. 10-12 illustrate additional flow diagrams of example, non-limiting methods that facilitate trusted pairing between an implantable device and an external device in accordance with one or more embodiments described herein.

Referring now to FIG. 10, shown is a flow diagram of an example method 1000 configured to facilitate trusted pairing between an implantable device and an external device in accordance with one embodiment. In some embodiments of method 1000, an implantable device (e.g., implantable device 104) employs a communication component (e.g., communication component 402), and a security component (e.g., security component 404) to facilitate trusted paring between the implantable device and an external device (e.g., external device 116) Repetitive description of like elements employed in other embodiments described herein is omitted for sake of brevity.

At 1002, an implantable medical device comprising a processor, initiates establishment of a trusted telemetry communication relationship with an external device in accordance with a defined telemetry protocol based on reception of a request, from the external device, to establish the trusted telemetry communication relationship with the implantable medical device using the defined telemetry protocol. At 1004, the implantable device restricts the establishment of the trusted telemetry communication relationship with the external device in accordance with the defined telemetry protocol based on reception of validation information from the external device, wherein provision of the validation information is supplementary to the defined telemetry protocol.

Turning now to FIG. 11, shown is a flow diagram of another example method 1100 configured to facilitate trusted pairing between an implantable device and an external device in accordance with one embodiment. In some embodiments of method 1100, an implantable device (e.g., implantable device 104) employs a communication component (e.g., communication component 402), and a security component (e.g., security component 404) to facilitate trusted paring between the implantable device and an external device (e.g., external device 116) Repetitive description of like elements employed in other embodiments described herein is omitted for sake of brevity.

At 1102, an implantable medical device comprising a processor, receiving a request from an external device to establish a telemetry link with implantable medical device using a telemetry protocol. At 1104, based on the receiving the request, the implantable medical device determines whether the external device is associated with data in memory of the implantable medical device that characterizes the external device as a trusted device, wherein association of the external device with the data indicates the implantable device previously received validation information from the external device in association with a pairing procedure performed between the implantable medical device and the external device according to the telemetry protocol, and wherein the validation information is not defined by the telemetry protocol.

FIG. 12 shows a flow diagram of another example method 1200 configured to facilitate trusted pairing between an implantable device and an external device in accordance with one embodiment. In some embodiments of method 1200, an external device (e.g., external device 116) employs a communication component (e.g., communication component 904), a connection request component (e.g., connection request component 906) and a pairing component (e.g., pairing component 908) to facilitate trusted paring between the external device and the implantable device (e.g., implantable device 104). Repetitive description of like elements employed in other embodiments described herein is omitted for sake of brevity.

At 1202, a device comprising a processor (e.g., external device 116) sends a request to pair with an implantable medical device using a defined telemetry protocol. At 1204, the device generates validation information based on the sending the request, wherein the validation information is not defined by the defined telemetry protocol. At 1206, the device provides the validation information to the implantable device, and at 1208, the device receives confirmation that the device is successfully paired with the implantable device based on a determination that the validation information is as associated with authorization information indicating authorization to pair with the implantable device.

Figure 13:
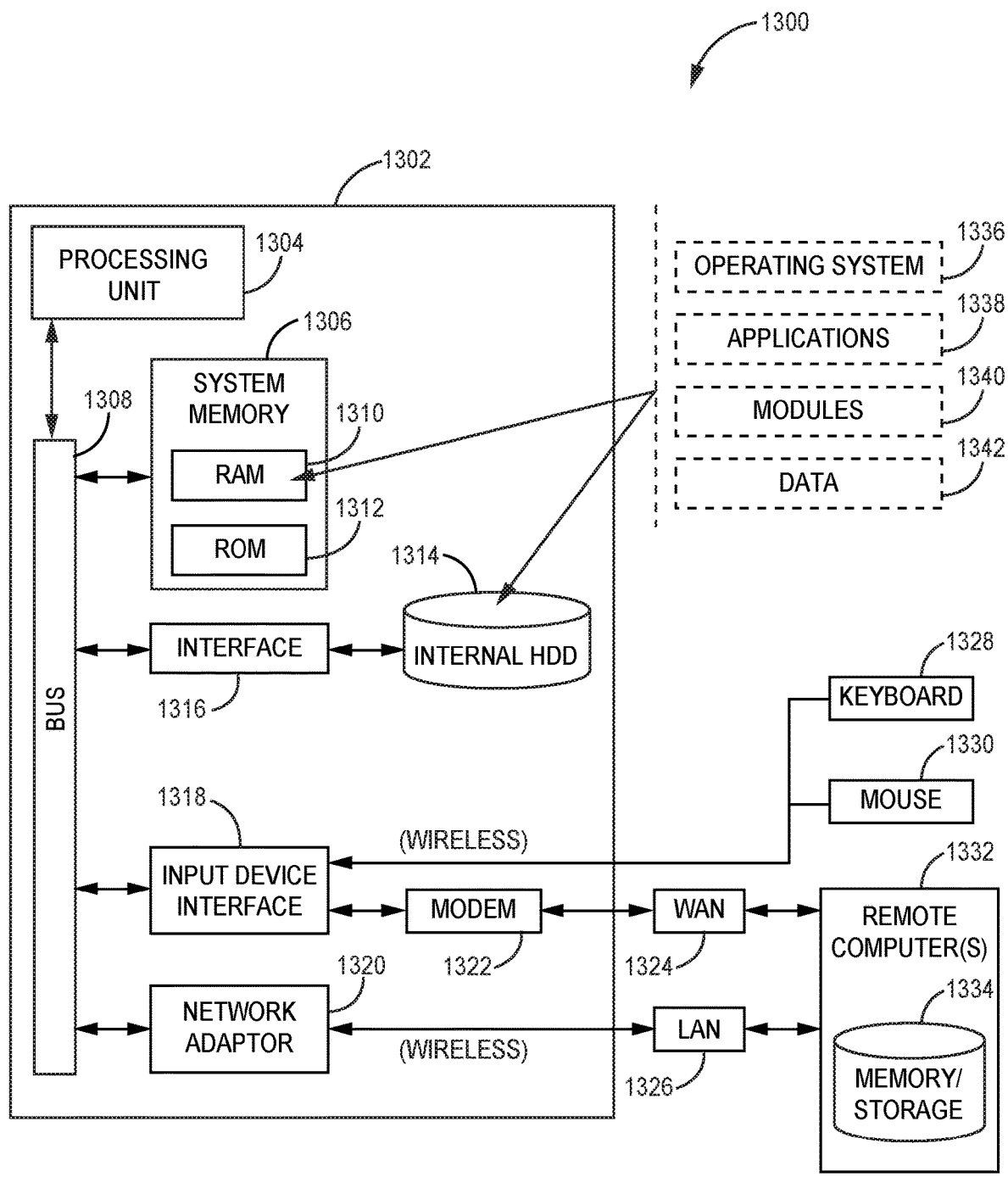
FIG. 13 illustrates a block diagram of an example, non-limiting computer operable to facilitate trusted pairing between an implantable device and an external device in accordance with one or more embodiments described herein.

FIG. 13 illustrates a block diagram of an example, non-limiting computer operable to facilitate telemetry overuse reduction in an implantable device in accordance with one or more embodiments described herein. For example, in some embodiments, the computer can be or be included within implantable device 104 and/or external device 116. Repetitive description of like elements employed in other embodiments described herein is omitted for sake of brevity.

In order to provide additional context for one or more embodiments described herein, FIG. 13 and the following discussion are intended to provide a brief, general description of a suitable computing environment 1300 in which the one or more embodiments described herein can be implemented.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

Computing devices typically include a variety of media, which can include computer-readable storage media and/or communications media, which two terms are used herein differently from one another as follows. Computer-readable storage media can be any available storage media that can be accessed by the computer and includes both volatile and nonvolatile media, removable and non-removable media. By way of example, and not limitation, computer-readable storage media can be implemented in connection with any method or technology for storage of information such as computer-readable instructions, program modules, structured data or unstructured data. Tangible and/or non-transitory computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD) or other optical disk storage, magnetic cassettes, magnetic tape, magnetic disk storage, other magnetic storage devices and/or other media that can be used to store desired information. Computer-readable storage media can be accessed by one or more local or remote computing devices, e.g., via access requests, queries or other data retrieval protocols, for a variety of operations with respect to the information stored by the medium.

In this regard, the term "tangible" herein as applied to storage, memory, computer-readable media or computer-readable storage media, is to be understood to exclude only propagating intangible signals per se as a modifier and does not relinquish coverage of all standard storage, memory, computer-readable media or computer-readable storage media that are not only propagating intangible signals per se.

In this regard, the term "non-transitory" herein as applied to storage, memory, computer-readable media or computer-readable storage media, is to be understood to exclude only propagating transitory signals per se as a modifier and does not relinquish coverage of all standard storage, memory, computer-readable media or computer-readable storage media that are not only propagating transitory signals per se.

Communications media typically embody computer-readable instructions, data structures, program modules or other structured or unstructured data in a data signal such as a modulated data signal, e.g., a channel wave or other transport mechanism, and includes any information delivery or transport media. The term "modulated data signal" or signals refers to a signal that has one or more of the data signal's characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 13, example environment 1300 that can be employed to implement one or more embodiments of the embodiments described herein includes computer 1302. Computer 1302 includes processing unit 1304, system memory 1306 and system bus 1308. System bus 1308 couples system components including, but not limited to, system memory 1306 to processing unit 1304. Processing unit 1304 can be any of various commercially available processors. Dual microprocessors and other multi-processor architectures can also be employed as processing unit 1304.

System bus 1308 can be any of several types of bus structure that can further interconnect to a memory bus (with or without a memory controller), a peripheral bus, and a local bus using any of a variety of commercially available bus architectures. System memory 1306 includes RAM 1310 and ROM 1312. A basic input/output system (BIOS) can be stored in a non-volatile memory such as ROM, erasable programmable read only memory (EPROM), EEPROM, which BIOS contains the basic routines that help to transfer information between elements within computer 1302, such as during startup. RAM 1310 can also include a high-speed RAM such as static RAM for caching data.

Computer 1302 further includes internal hard disk drive (HDD) 1314 (e.g., Enhanced Integrated Drive Electronics (EIDE), Serial Advanced Technology Attachment (SATA)). HDD 1314 can be connected to system bus 1308 by hard disk drive interface 1316. The drives and their associated computer-readable storage media provide nonvolatile storage of data, data structures, computer-executable instructions, and so forth. For computer 1302, the drives and storage media accommodate the storage of any data in a suitable digital format.

A number of program modules can be stored in the drives and RAM 1310, including operating system 1336, one or more application programs 1338, other program modules 1340 and program data 1342. All or portions of the operating system, applications, modules, and/or data can also be cached in RAM 1310. The systems and methods described herein can be implemented utilizing various commercially available operating systems or combinations of operating systems.

A mobile device can enter commands and information into computer 1302 through one or more wireless input devices, e.g., wireless keyboard 1328 and a pointing device, such as wireless mouse 1330. Other input devices (not shown) can include a smart phone, tablet, laptop, wand, wearable device or the like. These and other input devices are often connected to the processing unit 1304 through input device interface 1318 that can be coupled to system bus 1308, but can be connected by other interfaces, such as a parallel port, an IEEE serial port, a game port and/or a universal serial bus (USB) port.

Computer 1302 can operate in a networked environment using logical connections via wired and/or wireless communications to one or more remote computers, such as remote computer(s) 1332. Remote computer(s) 1332 can be a workstation, a server computer, a router, a personal computer, portable computer, microprocessor-based entertainment appliance, a peer device or other common network node, and typically includes many or all of the elements described relative to computer 1302, although, for purposes of brevity, only memory/storage device 1334 is illustrated. The logical connections depicted include wired/wireless connectivity to a local area network (LAN) 1326 and/or larger networks, e.g., WAN 1324, as well as smaller PANs involving a few devices (e.g., at least two). LAN and WAN networking environments are commonplace in the home, offices (e.g., medical facility offices, hospital offices) and companies, and facilitate enterprise-wide computer networks, such as intranets, all of which can connect to a global communications network (e.g., the Internet).

When used in a LAN networking environment, computer 1302 can be connected to local network through a wired and/or wireless communication network interface or adapter 1320. Adapter 1320 can facilitate wired or wireless communication to LAN 1326, which can also include a wireless access point (AP) connected to the LAN 1326 for communicating with adapter 1320.

When used in a WAN networking environment, computer 1302 can include modem 1322 or can be connected to a communications server on WAN 1324 or has other apparatus for establishing communications over WAN 1324, such as by way of the Internet. Modem 1322, which can be internal or external and a wired or wireless device, can be connected to system bus 1308 via input device interface 1318. In a networked environment, program modules depicted relative to computer 1302 or portions thereof, can be stored in a remote memory/storage device. It will be appreciated that the network connections shown are example and other apparatus of establishing a communications link between the computers can be used.

Computer 1302 can be operable to communicate with any wireless devices or entities operatively disposed in wireless communication via any number of protocols, including, but not limited to, NFC, Wi-Fi and/or BLUETOOTH® wireless protocols. Thus, the communication can be a defined structure as with a conventional network or simply an ad hoc communication between at least two devices.

NFC can allow point-to-point connection to an NFC-enabled device in the NFC field of an IMD within the home or at any location. NFC technology can be facilitated using an NFC-enabled smart phone, tablet or other device that can be brought within 3-4 centimeters of an implanted NFC component. NFC typically provides a maximum data rate of 424 kilobits per second (Kbps), although data rates can range from 6.67 Kbps to 828 Kbps. NFC typically operates at the frequency of 13.56 megahertz (MHz). NFC technology communication is typically over a range not exceeding 0.2 meters (m) and setup time can be less than 0.1 seconds. Low power (e.g., 13 milliamperes (mAs)) reading of data can be performed by an NFC device.

Wi-Fi can allow connection to the Internet from a couch at home, a bed in a hotel room or a conference room at work, without wires. Wi-Fi is a wireless technology similar to that used in a cell phone that enables such devices, e.g., computers, to send and receive data indoors and out. Wi-Fi networks use radio technologies called IEEE 802.11 (a, b, g, n, etc.) to provide secure, reliable, fast wireless connectivity. A Wi-Fi network can be used to connect computers to each other, to the Internet, and to wired networks (which can use IEEE 802.3 or Ethernet). Wi-Fi networks operate in the unlicensed 2.4 and 5 GHz radio bands, at an 11 Mbps (802.11a) or 54 Mbps (802.11b) data rate, for example or with products that contain both bands (dual band), so the networks can provide real-world performance similar to the basic 10BaseT wired Ethernet networks used in many offices.

The embodiments of devices described herein can employ artificial intelligence (AI) to facilitate automating one or more features described herein. The embodiments (e.g., in connection with automatically identifying acquired cell sites that provide a maximum value/benefit after addition to an existing communication network) can employ various AI-based schemes for carrying out one or more embodiments thereof. Moreover, the classifier can be employed to determine a ranking or priority of each cell site of an acquired network. A classifier is a function that maps an input attribute vector, x=(x1, x2, x3, x4, . . . , xn), to a confidence that the input belongs to a class, that is, f(x)=confidence (class). Such classification can employ a probabilistic and/or statistical-based analysis (e.g., factoring into the analysis utilities and costs) to prognose or infer an action that a mobile device desires to be automatically performed. A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated, one or more of the embodiments can employ classifiers that are explicitly trained (e.g., via a generic training data) as well as implicitly trained (e.g., via observing mobile device behavior, operator preferences, historical information, receiving extrinsic information). For example, SVMs can be configured via a learning or training phase within a classifier constructor and feature selection module. Thus, the classifier(s) can be used to automatically learn and perform a number of functions, including but not limited to determining according to a predetermined criteria which of the acquired cell sites will benefit a maximum number of subscribers and/or which of the acquired cell sites will add minimum value to the existing communication network coverage, etc.

As employed herein, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components or any combination thereof designed to perform the functions described herein. Processors can exploit nano-scale architectures such as, but not limited to, molecular and quantum-dot based transistors, switches and gates, in order to optimize space usage or enhance performance of mobile device equipment. A processor can also be implemented as a combination of computing processing units.

Memory disclosed herein can include volatile memory or nonvolatile memory or can include both volatile and nonvolatile memory. By way of illustration, and not limitation, nonvolatile memory can include ROM, programmable ROM (PROM), electrically programmable ROM (EPROM), electrically erasable PROM (EEPROM) or flash memory. Volatile memory can include RAM, which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). The memory (e.g., data storages, databases) of the embodiments is intended to include, without being limited to, these and any other suitable types of memory As used herein, terms such as "data storage," "database," and substantially any other information storage component relevant to operation and functionality of a component, refer to "memory components," or entities embodied in a "memory" or components including the memory. It will be appreciated that the memory components or computer-readable storage media, described herein can be either volatile memory or nonvolatile memory or can include both volatile and nonvolatile memory.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word "example" or "exemplary" is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application should generally be construed to mean "one or more" unless specified otherwise or clear from context to be directed to a singular form. The terms "first," "second," "third," and so forth, as used in the claims and description, unless otherwise clear by context, is for clarity only and doesn't necessarily indicate or imply any order in time.

What has been described above includes mere examples of one or more embodiments. It is, of course, not possible to describe every conceivable combination of components or methodologies for purposes of describing these examples, but one of ordinary skill in the art can recognize that many further combinations and permutations of the present embodiments are possible. Accordingly, the embodiments disclosed and/or claimed herein are intended to embrace all such alterations, modifications and variations that fall within the spirit and scope of the detailed description and the appended claims. Furthermore, to the extent that the term "includes" is used in either the detailed description or the claims, such term is intended to be inclusive in a manner similar to the term "comprising" as "comprising" is interpreted when employed as a transitional word in a claim.

The invention claimed is:

1. A method comprising:
 initiating, by an implantable medical device comprising a processor, establishment of a trusted telemetry communication relationship with an external device in accordance with a defined telemetry protocol based on reception of a request, from the external device, to establish the trusted telemetry communication relationship with the implantable medical device using the defined telemetry protocol;
 based on reception of the request, negotiating, by the implantable medical device, one or more encryption keys with the external device in accordance with the defined telemetry protocol;
 associating, by the implantable medical device, the one or more encryption keys and an identifier for the external device with first data in a memory of the implantable medical device that characterizes the external device as potentially authorized to establish the trusted telemetry communication relationship with the implantable medical device in accordance with the defined telemetry protocol; and
 restricting, by the implantable medical device, the establishment of the trusted telemetry communication relationship with the external device in accordance with the defined telemetry protocol based on reception of validation information from the external device, wherein provision of the validation information is supplementary to the defined telemetry protocol.

2. The method of claim 1, wherein the establishment of the trusted telemetry communication relationship comprises negotiation of security information between the implantable medical device and the external device, and wherein based on the establishment of the trusted telemetry communication relationship, the implantable medical device is configured to accept requests from the external device to establish telemetry connections with the implantable medical device using the defined telemetry protocol without negotiating new security information and without requiring the external device to provide the validation information or new validation information.

3. The method of claim 1, wherein the validation information indicates a remote server verified the external device or an entity operating the external device as being authorized to establish the trusted telemetry communication relationship with the implantable medical device.

4. The method of claim 1, wherein the validation information indicates an application of the external device determined an entity operating the external device is authorized to employ the external device to establish the trusted telemetry communication relationship with the implantable medical device.

5. The method of claim 4, wherein the application is configured to determine the entity is authorized based on reception of input, via the external device, that uniquely identifies the entity as an authorized entity.

6. The method of claim 1, further comprising:
based on reception of the validation information, establishing, by the implantable medical device, the trusted telemetry communication relationship with the external device by associating the one or more encryption keys and the identifier with second data in the memory that characterizes the external device as a trusted device.

7. The method of claim 6, further comprising:
disassociating, by the implantable medical device, the one or more encryption keys and the identifier from the second data based on reception of the validation information or new validation information in association with a new request to remove the external device from the second data, wherein the new validation information is not defined by the defined telemetry protocol.

8. A non-transitory computer readable medium comprising computer executable instructions that, in response to execution, cause an implantable medical device including at least one processor to perform operations comprising:
receiving a request from an external device to establish a telemetry link with the implantable medical device using a defined telemetry protocol; and
based on the receiving the request, negotiating one or more encryption keys with the external device in accordance with the defined telemetry protocol, associating the one or more encryption keys and an identifier for the external device with first data in a memory which characterizes the external device as potentially authorized to establish the trusted telemetry communication relationship with the implantable medical device in accordance with the defined telemetry protocol, and determining whether the external device is associated with the first data in the memory of the implantable medical device that characterizes the external device as a trusted device, wherein association of the external device with the first data indicates the implantable medical device previously received validation information from the external device in association with a pairing procedure performed between the implantable medical device and the external device according to the defined telemetry protocol, restricting the establishment of the trusted telemetry communication relationship with the external device in accordance with the defined telemetry protocol based on reception of validation information from the external device, and wherein the validation information is supplementary to the defined telemetry protocol.

9. The non-transitory computer readable medium of claim 8, further comprising:
establishing the telemetry link with the external device using the defined telemetry protocol based on a determination that the external device is associated with the first data.

10. The non-transitory computer readable medium of claim 8, further comprising:
forgoing establishing the telemetry link with the external device based on a determination that the external device is not associated with the first data.

11. The non-transitory computer readable medium of claim 8, wherein the validation information indicates a remote server verified the external device or an entity operating the external device as being authorized to establish a trusted telemetry communication relationship with the implantable medical device.

12. The non-transitory computer readable medium of claim 8, wherein the validation information indicates an application of the external device determined an entity operating the external device is authorized to employ the external device to establish a trusted telemetry communication relationship with the implantable medical device.

13. The non-transitory computer readable medium of claim 12, wherein the application is configured to determine the entity is authorized based on reception of input, via the external device, that uniquely identifies the entity as an authorized entity.

* * * * *